United States Patent
Maitra et al.

(10) Patent No.: US 10,614,196 B2
(45) Date of Patent: Apr. 7, 2020

(54) SYSTEM FOR AUTOMATED ANALYSIS OF CLINICAL TEXT FOR PHARMACOVIGILANCE

(71) Applicant: Accenture Global Services Limited, Dublin (IE)

(72) Inventors: Anutosh Maitra, Bangalore (IN); Annervaz Karukapadath Mohamedrasheed, Trichur (IN); Tom Geo Jain, Bangalore (IN); Madhura Shivaram, Bangalore (IN); Shubhashis Sengupta, Bangalore (IN); Roshni Ramesh Ramnani, Bangalore (IN); Neetu Pathak, Bangalore (IN); Debapriya Banerjee, Hooghly (IN); Vedamati Sahu, Bangalore (IN)

(73) Assignee: Accenture Global Services Limited, Dublin (IE)

(*) Notice: Subject to any disclaimer, the term of this patent is extended or adjusted under 35 U.S.C. 154(b) by 1092 days.

(21) Appl. No.: 14/826,575

(22) Filed: Aug. 14, 2015

(65) Prior Publication Data
US 2016/0048655 A1  Feb. 18, 2016

(30) Foreign Application Priority Data

Aug. 14, 2014 (IN) ............ 3984/CHE/2014
Aug. 26, 2014 (IN) ............ 4173/CHE/2014
Jul. 2, 2015 (IN) ............ 3984/CHE/2014

(51) Int. Cl.
*G16H 50/20* (2018.01)
*G16H 20/10* (2018.01)
(Continued)

(52) U.S. Cl.
CPC ........ *G06F 19/3456* (2013.01); *G06F 19/326* (2013.01); *G16H 10/20* (2018.01);
(Continued)

(58) Field of Classification Search
None
See application file for complete search history.

(56) References Cited

U.S. PATENT DOCUMENTS 7,461,006 B2  12/2008  Gogolak
2002/0082868 A1  6/2002  Pories et al.
(Continued)

FOREIGN PATENT DOCUMENTS

WO  WO 2009/039230 A2  3/2009

OTHER PUBLICATIONS

Styler et al., THYME (Temporal Histories of Your Medical Events) Temporal Relations Annotation Guidelines, Feb. 14, 2015, http://wstyler.ucsd.edu/files/THYMEGuidelines.pdf (Year: 2014).*

(Continued)

*Primary Examiner* — Devin C Hein
(74) *Attorney, Agent, or Firm* — Brinks Gilson & Lione

(57) ABSTRACT

In the pharmaceutical research and development process, it may be necessary to process large amounts of medical records or clinical literature, to ensure safety of patients consuming a drug. A pharmacovigilance system may assist in this process by efficiently and automatically processing medical records to extract information and relationships contained therein and may also form a preliminary assessment regarding a medical or clinical judgment. The pharmacovigilance system may automatically generate reports based on this information, which may be validated by trained clinicians and medical experts.

17 Claims, 14 Drawing Sheets

(51) Int. Cl.
  *G16H 15/00* (2018.01)
  *G16H 50/70* (2018.01)
  *G06F 19/00* (2018.01)
  *G16H 10/20* (2018.01)
(52) U.S. Cl.
  CPC ............ *G16H 15/00* (2018.01); *G16H 20/10* (2018.01); *G16H 50/20* (2018.01); *G16H 50/70* (2018.01); *Y02A 90/26* (2018.01)

(56) References Cited

U.S. PATENT DOCUMENTS

| | | |
|---|---|---|
| 2002/0165853 A1 | 11/2002 | Gogolak |
| 2007/0214009 A1 | 9/2007 | Epstein et al. |
| 2009/0099870 A1 | 4/2009 | Wilkinson et al. |
| 2009/0119095 A1 | 5/2009 | Beggelman |
| 2010/0324927 A1 | 12/2010 | Tinsley |
| 2012/0233215 A1* | 9/2012 | Walker ............... G06F 19/328 707/777 |
| 2013/0041685 A1 | 2/2013 | Yegnanarayanan |
| 2013/0073554 A1 | 3/2013 | Bachert et al. |
| 2013/0124523 A1 | 5/2013 | Rogers et al. |
| 2014/0006013 A1 | 1/2014 | Markatou et al. |
| 2014/0046696 A1 | 2/2014 | Higgins |
| 2014/0058744 A1 | 2/2014 | Nadarajah et al. |
| 2015/0081323 A1 | 5/2015 | Jackson et al. |
| 2016/0048655 A1 | 2/2016 | Maitra et al. |
| 2017/0228500 A1 | 8/2017 | Massengale |
| 2017/0293725 A1 | 10/2017 | Liu et al. |
| 2017/0329900 A1 | 11/2017 | Kato et al. |
| 2017/0351830 A1 | 12/2017 | Burger et al. |
| 2018/0082197 A1 | 3/2018 | Aravamudan et al. |
| 2018/0089381 A1 | 3/2018 | Allen et al. |
| 2018/0089568 A1 | 3/2018 | Allen |
| 2018/0101598 A1 | 4/2018 | Allen et al. |

OTHER PUBLICATIONS

Extended European Search Report from corresponding European Application No. 15181099.1, 10pp, Jan. 19, 2016.
European Office Action, dated Dec. 20, 2016, pp. 1-13, issued in European Patent Application No. 15 181 099.1, European Patent Office, Munich, Germany.
Australian Examination Report 1, dated Aug. 5, 2016, pp. 1-3, issued in Australian Patent Application No. 2015213399, IP Australia, Woden, ACT, Australia.
Australian Examination Report 2, dated Jan. 11, 2017, pp. 1-4, issued in Australian Patent Application No. 2015213399, IP Australia, Woden, ACT, Australia.
Australian Examination Report 3, dated May 24, 2017, pp. 1-4, issued in Australian Patent Application No. 2015213399, IP Australia, Woden, ACT, Australia.
Examination Report No. 1 for Australia Application No. 2017210493, dated Oct. 4, 2018, pp. 1-6, IP Australia, Phillip, Australia.
Examination Report No. 4 for Australia Application No. 2015213399, dated Jul. 26, 2017, pp. 1-6, IP Australia, Phillip, Australia.
Alan R. Aronson et al., "An overview of MetaMap: historical perspective and recent advances," dated May 4, 2010, pp. 1-9, published by JAMIA at group.bmj.com.
Youngduck Choi et al., "Learning Low-Dimensional Representations of Medical Concepts," AMIA Summits on Translational Science Proceedings, dated Jul. 20, 2016, pp. 1-10, published online by American Medical Informatics Association.
Examination Report No. 1, issued in Australian Application No. 2018202580, pp. 1-5, dated Jun. 20, 2018, IP Australia, Phillip, Australia.
Examination Report No. 2, issued in Australian Application No. 2017210493, dated Jul. 10, 2019, pp. 1-5, IP Australia, Phillip, Australia.
Notice of Allowance, issued in U.S. Appl. No. 15/637,821, dated Apr. 9, 2019, pp. 1-11, U.S. Patent and Trademark Office, Alexandria, VA.
Examination Report No. 2, issued in Australian Application No. 2018202580, dated Jan. 3, 2019, pp. 1-2, IP Australia, Phillip, Australia.
Notice of Acceptance, issued in Australian Application No. 2018202580, dated Feb. 13, 2019, pp. 1-3, IP Australia, Phillip, Australia.
Examination Report No. 3, issued in Australian Application No. 2017210493, dated Oct. 1, 2019, pp. 1-5, IP Australia, Phillip, Australia.

* cited by examiner

The pregnant patient had history of abortion. She was started on
       701⌐        702⌐
drug X. On 26-Aug-2013, fetal heart rate decrease developed.
                         704⌐
Because of prolonged pregnancy, the mother was planned for
705⌐                             701⌐
induction, which was then done with metronidazole monotherapy. On
703⌐                                703⌐
27-Aug-2013, the patient had 15 min-contraction intervals.
Thereafter, the delivery was successful and feeding was promptly
705⌐           703⌐
started for hypoglycemia
            704⌐

Drug X (given for) history of abortion
Drug X (happened before) fetal heart decrease
Drug X (happened before) hypoglycemia of newborn

SYSTEM FOR AUTOMATED ANALYSIS OF CLINICAL TEXT FOR PHARMACOVIGILANCE

RELATED APPLICATIONS

This application claims the benefit of priority to: Indian Provisional Patent Application Ser. No. 3984/CHE/2014, filed on Aug. 14, 2014 and entitled "TEXT ANALYSIS PLATFORM FOR PHARMACOVIGILANCE OF CLINICAL DRUGS"; Indian Provisional Patent Application Ser. No. 4173/CHE/2014, filed on Aug. 26, 2014, and entitled "SYSTEM FOR AUTOMATED ANALYSIS OF CLINICAL DATA FOR PHARMACOVIGILANCE"; and Indian Non-Provisional Patent Application Ser. No. 3984/CHE/2014, filed on Jul. 2, 2015 and entitled "SYSTEM FOR AUTOMATED ANALYSIS OF CLINICAL TEXT FOR PHARMACOVIGILANCE," which are incorporated by reference herein in their entirety.

TECHNICAL FIELD

This disclosure relates to a system and method in which medical data is automatically processed and analyzed in order to identify potential effects associated with the use of a particular drug or treatment regimen.

BACKGROUND

Pharmacovigilance (PV), also known as Drug Safety Surveillance, is the pharmacologic science relating to the collection, detection, assessment, monitoring, and prevention of adverse effects with pharmaceutical products. This is an important process that allows regulatory authorities to continue to assess benefits and risks throughout the lifecycle of a drug and potentially detect serious adverse events and identify new drug safety signals that were previously undetected by typical marketing authorization. The process generally involves medical information, which can be received from patients, healthcare providers, medical literature, physicians, pharmaceutical company's sales team, pharmacists, or the like. Information collected from different sources needs to be processed in a defined consistent way for electronic submission to the regulatory authorities like FDA (Food and Drug Authority), WHO (World Health Organization), MHRA (Medicines and Health Regulatory Agency), EMA (European Medicines Agency) and other local authorities. Apart from regulatory requirements, pharmaceutical companies need to engage in pharmacovigilance to serve public health, and to foster a sense of trust with patients who used the drug, and to proactively monitor drug effects to prevent product withdrawal from market due to safety issues.

Maintaining a robust pharmacovigilance system relies on consistent and accurate acquisition, integration and analysis of adverse event data. Without a strong foundation, important safety signals may not be fully identified and evaluated. Some studies estimate that as much as 30% of all drug reactions result from concomitant use and that an estimated 29.4% of elderly patients are on six or more drugs. Several published drug-safety papers have shown that adverse effects of drugs may be detected too late when millions of patients have already been exposed to them. For a long time, researchers have been seeking a real time, continuous and prospective approach that could integrate vast, dispersed and unstructured information and knowledge bases to obtain unambiguous drug reaction relationships to automate the narrative generation process. However, for a single patient, this may require processing numerous medical records, which can be a time consuming process requiring the expertise of medical professionals. The difficulty in maintaining vigilance over a drug's effect on patients is further compounded by the fact that the drug may be given to large patient populations, both during trial and once on the market. Furthermore, government regulatory agencies, such as the FDA, require prompt and detailed reporting of this information.

As mentioned above, analyzing possible drug safety incidents and generating narratives in the pharmacovigilance process have traditionally relied upon manual review of case reports from patients, consumers and healthcare professionals, which may involve literature searching, case screening, case processing, narrative generation, and medical review. However, due to the vast quantity and complexity of data to be analyzed and the need for ensuring timeliness, reduced costs, and consistency and quality of reporting, such methods are not well suited and are generally time consuming and expensive. For instance, case processing and narrative generation may take several hours, and the medical review process may be iterative in nature requiring multiple reviews and several data lookups to establish causality. It may also be the case that there are not enough trained medical personnel to perform the task. Automating this process is also difficult given the volume of medical records that need to be processed and the fact that such data is provided in disparate formats. Additionally, meaningful analysis of the data requires identification of complex relationships that may not be readily apparent, even to trained professionals.

While computer-based systems have been developed to tackle this problem, existing computer-based systems only perform natural language processing in a limited capacity, and such systems are simply unable to investigate the relationships between the drugs, diseases (manifested through their system organ classes) and reactions in a sufficiently robust and complex automated fashion. The pharmacovigilance system described below seeks to address the limitations of current computer-based systems.

In particular, traditional computer-based systems are limited in their ability to identify relationships, in part, because the architecture of these systems and processes fail to account for the underlying clinical knowledge databases being disparate in their structure and management. Despite the need for a collaborative knowledge framework to automate the pharmacovigilance process through semantic integration of these databases, there has not been a successful effort within the industry to establish a relationship between multiple databases to assist the pharmacovigilance process.

Furthermore, given the limitations in traditional computer-based systems, substantial manual effort is still needed after processing the clinical text, for example, requiring manual look-up and review of different databases and manual identification of medical causation from these distinct data sources. However, because medical reviewers are often times familiar with only a handful of data sources and are prone to human error, manual identification of relationships in the clinical text is not always accurate or complete.

Furthermore, most of the text analytics based work in the pharmacovigilance domain has been restricted to academic and research purposes and address only a few of the sub-processes involved in the complete process chain. Complete end-to-end processing of adverse event (AE) reaction reports are typically unsupported by such systems. For the reasons noted above, human intervention can result in inconsistent, inaccurate and incomplete report generation, which has presented a huge hurdle in gaining the trust of end users and regulatory authorities.

While typical machine learning processes applying hidden Markov models or conditional random field analysis may seem suited for addressing some of these difficulties, such solutions have proven inadequate. Such methods have failed in part due to the unavailability of suitable annotated data, or the time and monetary expense required in creating such data. Moreover, in analogous contexts, it has been shown that the performance of machine learning methods is sub-optimal.

Accordingly, there is a need to provide a computer based system or method for processing large amounts of medical data quickly and efficiently to identify complex relationships between a particular drug or treatment regimen and the effects experienced by the user. The need is clear for collaborative and integrative approaches and strategies to allow faster identification of high-risk interactions between marketed drugs and adverse events, and to enable the automated uncovering of scientific evidence behind them.

SUMMARY

To overcome the limitations of conventional systems and processes, such as those noted above, the pharmacovigilance system described below is able to successfully aggregate the information provided in the various clinical knowledge databases in spite of their disparate structure, thereby allowing for the application of more robust natural language processing techniques that allow the system to more meaningfully process the clinical text. The described pharmacovigilance system is able to more accurately and completely capture relationships in the clinical text by leveraging multiple clinical knowledge databases in a systematic and automated fashion. The pharmacovigilance system also allows for dynamic integration of clinical knowledge databases and is able to adapt to, transform and incorporate new databases as they become available.

The pharmacovigilance system described below may be used to automatically process disparate source documents, which may be received from a variety of sources. The documents may be converted into a canonical format, from which the pharmacovigilance system may extract medical and non-medical text-tokens, which may be processed to identify semantic classes and semantic associations between the classes. The pharmacovigilance system may create temporal models and infer potential causal chains from the converted data by using the semantic classes and associations that were identified. The pharmacovigilance system may generate clinical and process related inferences by applying rules against the temporal model and causal chains. The pharmacovigilance system may generate a narrative report, based on the temporal models and causal chains, the clinical and process related inferences, and the extracted medical and non-medical text tokens.

Other embodiments of the systems, methods, features, and their corresponding advantages will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The described system for automatically processing and analyzing medical data may be better understood with reference to the following drawings and the corresponding description. The components in the figures are not necessarily to scale; instead, emphasis has been placed upon illustrating the principles of the invention. Moreover, in the figures, like reference numerals designate corresponding parts throughout the different views.

FIG. 7 illustrates an example of the causal relationship identification that may be performed by the pharmacovigilance system.

FIG. 10 illustrates a first example of an intelligent text analysis platform (ITAP) user interface that the pharmacovigilance system may provide.

FIG. 11 illustrates a second example of an intelligent text analysis platform (ITAP) user interface that the pharmacovigilance system may provide.

DETAILED DESCRIPTION OF THE PREFERRED EMBODIMENTS

The pharmacovigilance system described herein may also utilize aspects and features described in Indian patent application Ser. No. 1390/CHE/2014, filed Mar. 17, 2014, entitled SEMANTIC MODELING OF TEXTUAL REQUIREMENTS FOR AUTOMATED ANALYSIS AND ENGINEERING, which is commonly assigned and incorporated herein by reference in its entirety.

Figure 1:
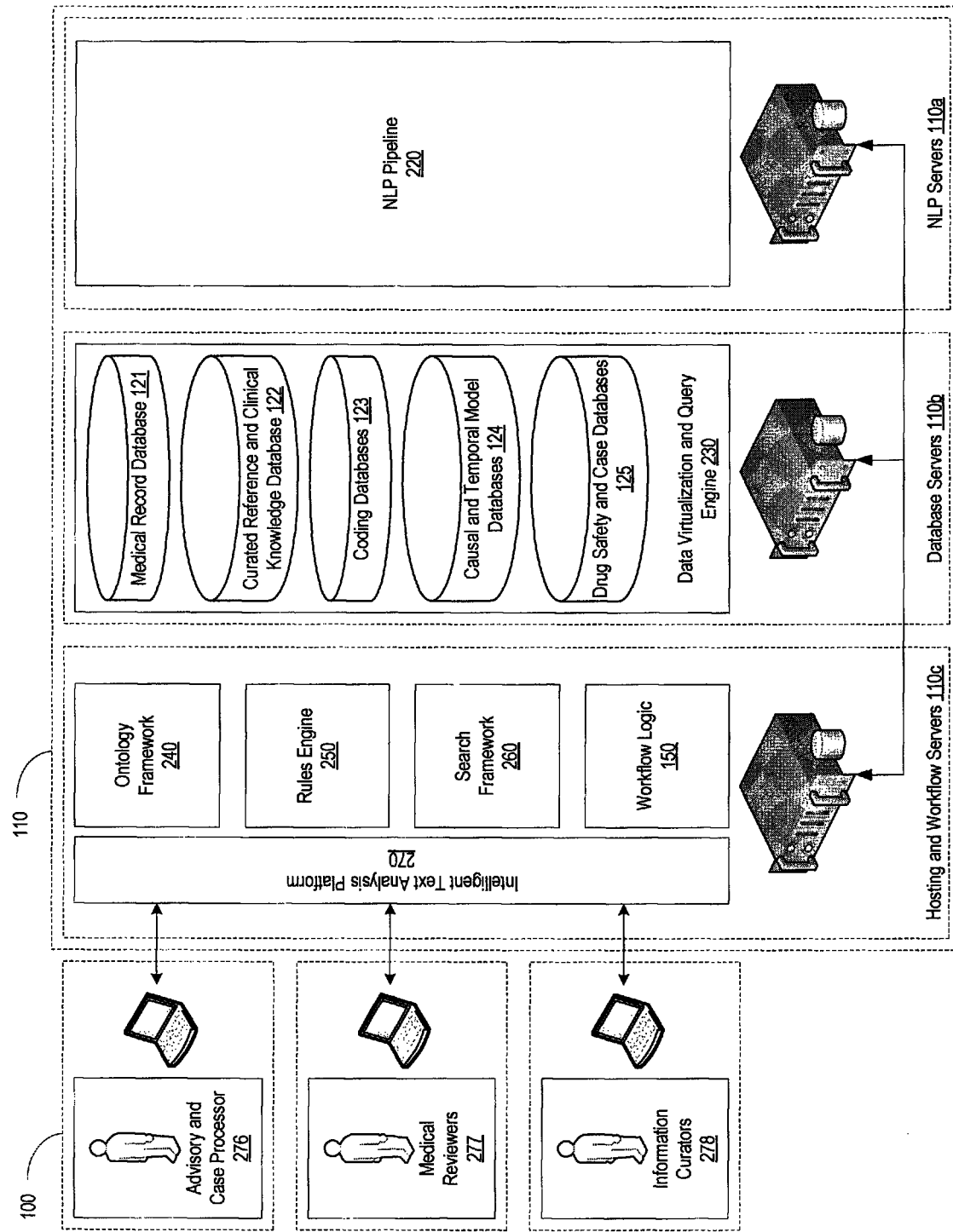
FIG. 1 provides an example of the system environment in which the pharmacovigilance system may operate.

FIG. 1 provides an example of the system environment in which the pharmacovigilance system may operate. The pharmacovigilance system 100 may include one or more servers 110, which may individually or collectively implement different functionality of the system. As an example, one set of servers 110a may be responsible for performing natural language processing functions, described in greater detail below, while another set of servers, for example, database servers 110b, may be responsible for handling the database interactions. The database servers 110b may interface with one or more databases 120, and may be responsible for maintaining and updating the databases 120. Additionally, or in the alternative, the databases 120 may be updated and maintained by a separate organization which the pharmacovigilance system 100 is able to access and interface with through the database servers 110b.

Continuing the example, another set of servers, for example web hosting and interfacing serves 110c, may be responsible for the web hosting and interfacing along with performing the necessary workflow logic. The web hosting and interfacing servers 110c may provide an intelligent text analysis platform (ITAP) 270 with which the users may interface.

In one embodiment, the pharmacovigilance system 100 may process medical records of patients involved in a clinical drug trial. The pharmacovigilance system 100, through automated understanding of bio-medical and clinical text, may provide causal analytics driven discovery of insights buried across the disparate information sources. The pharmacovigilance system 100 may receive documents from various disparate sources, which may contain documents in different formats and may contain structured or unstructured textual information. The documents may, for example, include medical records for a patient taking the drug. The pharmacovigilance system 100 may process these documents to extract information contained therein, and may further analyze the extracted information to make medical determinations. The pharmacovigilance system 100 may use the extracted information and the inferential determinations that are made to automatically generate reports regarding the documents that were processed. For example, the pharmacovigilance system 100 may automatically process patient records and generate reports mandated by various federal regulatory agencies. As a more specific example, the pharmacovigilance system 100 may generate adverse drug reaction reports mandated by the FDA, or other regulatory authorities, for drugs undergoing clinical trials. As it relates to medical literature, various studies may be conducted relating to a particular drug treatment or treatment regimen, which drug companies may be obligated to track, review and report to regulatory authorities. The pharmacovigilance system 100 may monitor medical literature databases (e.g., PubMed) to determine when new studies are published, and may automatically process the published Abstracts to determine if the study is relevant to a particular drug of interest. If the study is found to be relevant based on the analysis of the Abstract, further investigation may be warranted, and so the entire article may be ordered and processed by the pharmacovigilance system 100.

Processing the disparate source documents through the pharmacovigilance system 100 may provide various advantages, including, for example, a significant reduction in processing time, which may reduce the number of steps that are to be performed and streamline the report generation process. For instance, literature search may be largely automated, and case screening, triage, processing and narrative generation activities may be combined to provide aggregate time savings, for instance, a 40% reduction in total time spent. The pharmacovigilance system 100 may also reduce errors and produce more accurate reports as the medical review process may be augmented and supported through scientific inference and causal analytics. This too may result in significant efficiency gains, for example, resulting in improved efficiency in medical review (e.g., judging the seriousness of an event or proposing possible causal relationships between an event and a suspect drug), as efficiency in case processing is heavily dependent upon the ability of the medical professionals to quickly find out the causation chain based on their training, experience and access to available data resources.

The system may also integrate tools within the ITAP 270, which may facilitate human intervention in a seamless manner and may even serve to reduce the number of different human roles necessary for case processing. For instance, by using the ITAP 270, the pharmacovigilance system 100 may reduce the number of support roles needed, and may only require two types of users, a case processor or a narrative writer along with a medical reviewer, who are responsible for the complete adverse drug reaction detection and narrative generation process. Overall, the pharmacovigilance system 100 may be able to decrease the amount of time required for quality control and peer review, and may produce better quality reports with greater standardization.

While the foregoing description of the pharmacovigilance system 100 is made with reference to the medical information and pharmaceutical contexts, the pharmacovigilance system 100 is not so limited. The ability of the pharmacovigilance system 100 to perform complex inferences and intelligent decision making may be naturally extended to address similar problems in business, legal, and knowledge processes. The functionality of the pharmacovigilance system 100 may also be leveraged in the context of business analytics or social media analytics which may require the processing of text.

As it relates to information extraction, the pharmacovigilance system 100 may implement various natural language processing (NLP) methodologies, in an NLP pipeline 220. The NLP pipeline 220 may preprocess the source documents to convert them into a standard canonical format (e.g., XML), which may be better suited for applying NLP techniques. The NLP pipeline 220 of the pharmacovigilance system 100 may process the canonical data to identify different semantic classes along with relationships or associations between identified classes. The processing techniques of the NLP pipeline 220 may be enhanced by leveraging a plurality of medical databases 120, which provide a robust medical knowledge base upon which the system may draw.

The pharmacovigilance system 100 may further process this information to identify more global relationships, for example, identifying relationships between events throughout the document that form a temporal chain of events. For example, the pharmacovigilance system 100 may identify a chain of events connecting the consumption of a drug with an adverse event experienced by the patient. The pharmacovigilance system 100 may also use discourse parameters to infer potential causal links between these temporally ordered events. The pharmacovigilance system 100 may utilize a rules engine 250 to assess and confirm the presence of a causal link. Based on the information identified during processing, including the temporal and causal inferences that were made, the pharmacovigilance system 100 may generate a report, for example, based on a template for adverse drug reaction (ADR) reports.

Given that accuracy is paramount in such reports, the pharmacovigilance system 100 through the ITAP 270 may allow users to engage the system at various stages of processing, allowing for modification and validation by clinicians and medical experts. For example, in one embodiment, a user of the system may be able to manually identify semantic classes and relationships, add, remove, or rearrange events in a temporal or causal chain, validate medical and causal inferences, and revise the reports that are generated.

The pharmacovigilance process may follow a pipelined approach to processing medical information (e.g., drug safety reports generated in follow a pipelined approach to processing medical information (e.g., drug safety reports generated in the field), and may implement stage-wise processing through a client-server architecture. While the architecture may be implemented in a pipeline, it may also be event driven, in that different system events (e.g., user edits or updates) may be propagated throughout the system architecture, which may serve to invalidate certain computed data and trigger, or force, additional processing and reprocessing.

Figure 2:
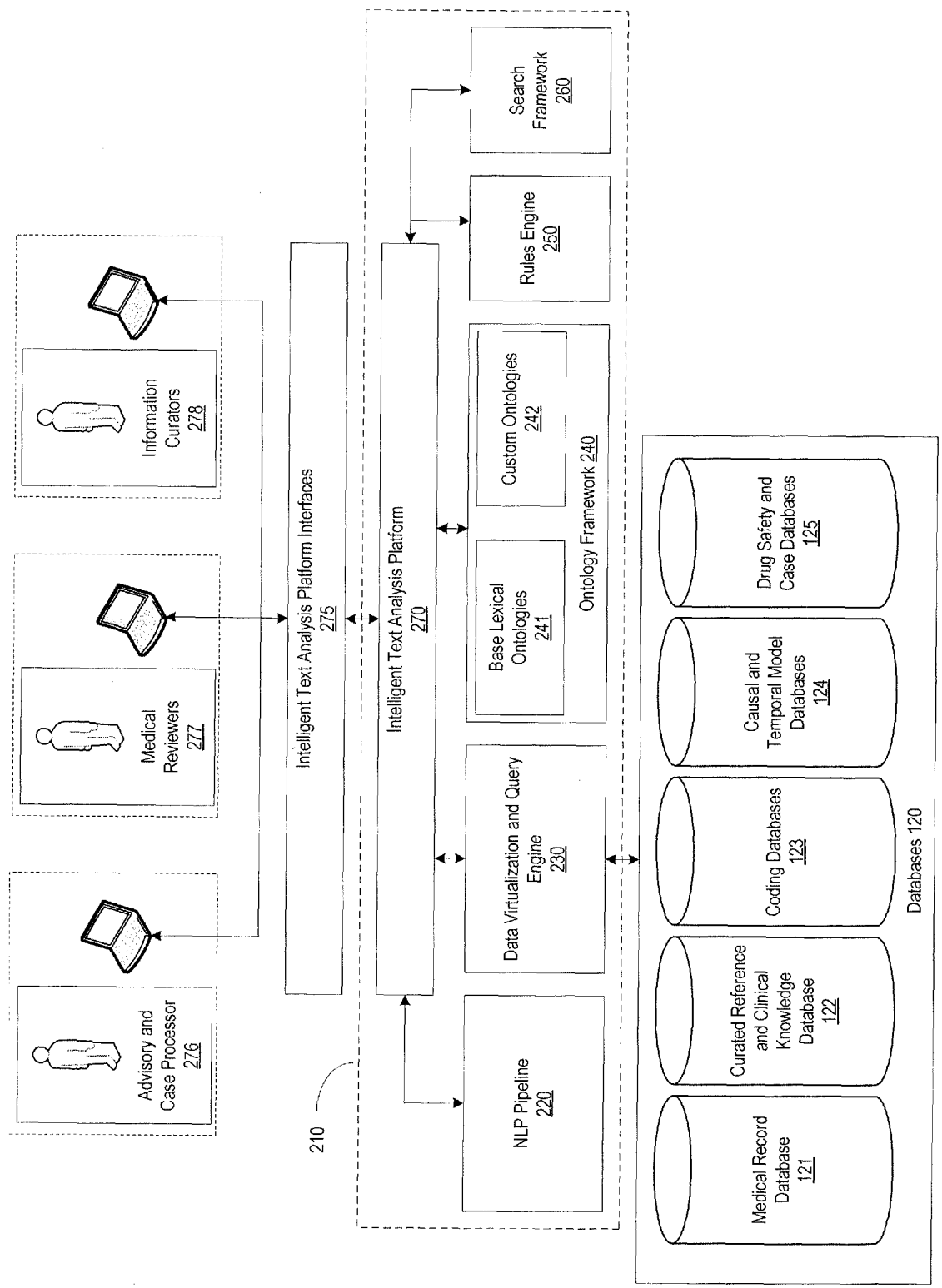
FIG. 2 provides an example of the system architecture on which the pharmacovigilance system may be implemented.
Figure 3:
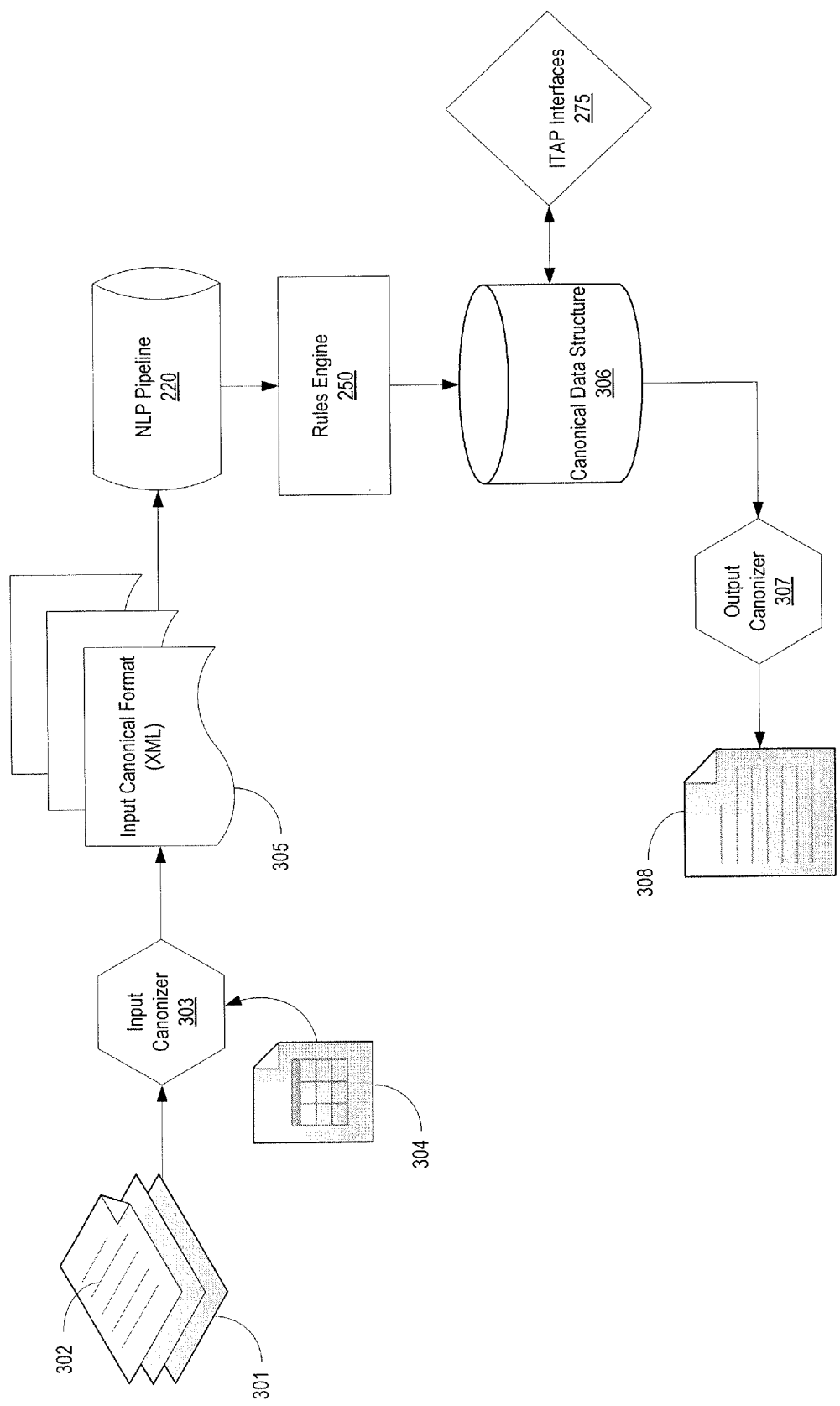
FIG. 3 illustrates, at a high level, the operation of an exemplary pharmacovigilance system.
Figure 4:
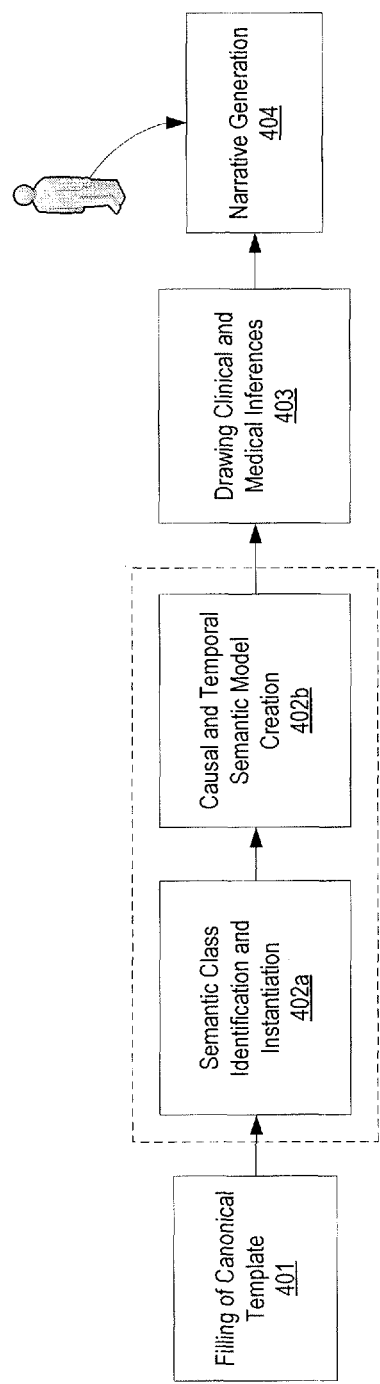
FIG. 4 describes, at a high level, the logic that may be implemented in a pharmacovigilance system.
Figure 5:
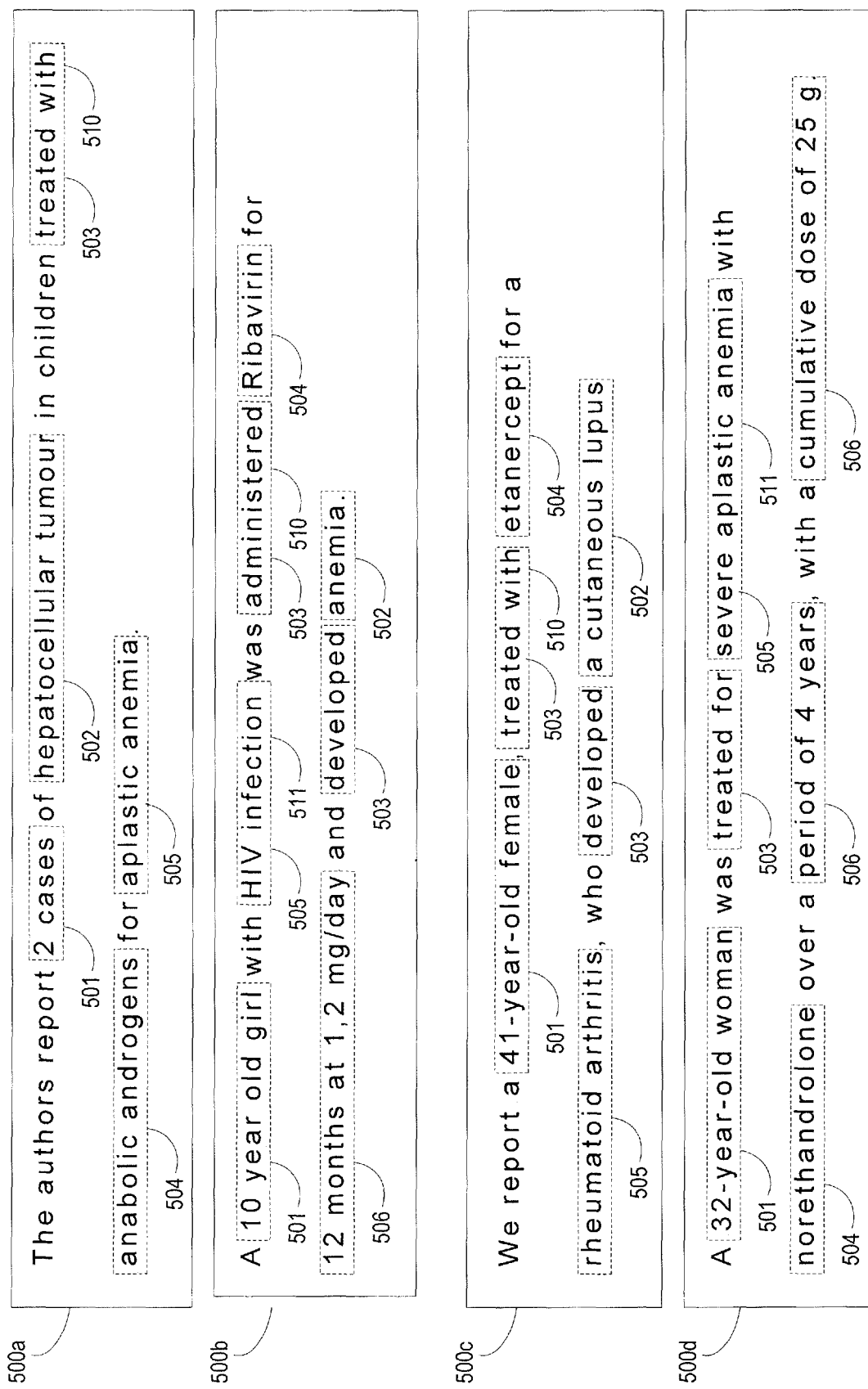
FIG. 5 illustrates an example of semantic class identification and semantic relationship recognition that may be performed by the pharmacovigilance system.

FIG. 2 provides an example of the system architecture on which the pharmacovigilance system 100 may be implemented, which may include a server stack 210, operating on the servers 110, and an intelligent text analysis platform (ITAP) 270. The server stack 210 of the pharmacovigilance system 100, for example, may implement a natural language processing (NLP) pipeline 220, a data virtualization and query engine 230, an ontology framework 240, a rules engine 250, and a search framework 260.

The pharmacovigilance system 100 may utilize the NLP pipeline 220 of the server stack 210 to analyze large volumes of structured or unstructured information. As an example, the NLP pipeline 220 may take the form of the Apache clinical Text Analysis and Knowledge Extraction System (cTAKES), or it may take the form of a generic dependency parser (like ClearNLP), or any other commercial natural language parsers, which are generally available and can be built upon Apache's Unstructured Information Management Architecture (UIMA), which is also available as an open-source product. The NLP pipeline 220 may perform one or more natural language processing functions, including text segmentation and sentence detection, pattern identification and substitution, sentence simplification, and coherent unit identification. The NLP pipeline 220 may also perform semantic class matching and domain restrained role labeling, and semantic attribute mapping and class consolidation and temporal anchoring and ordering and causal relationship identification.

In performing the one or more language processing functions, the NLP pipeline 220 may draw upon the ontology framework 240 and the data virtualization and query engine 230, which may allow the NLP pipeline to access one or more databases 120. For example, the NLP pipeline 220 may access one or more curated reference and clinical knowledge databases 122 and causal and temporal model databases 124, containing causal and temporal model templates, in performing the various language processing functions. Information input into the NLP pipeline 220 may be processed to generate structured representations of natural language text. The interaction between the NLP pipeline 220, the ontology framework 240 and data virtualization and query engine 230 to identify the different semantic classes and relationships, as described in greater detail below, provides an innovative approach to generating structured representations of natural language text. For example, by identifying different causal and temporal discourse markers the pharmacovigilance system may be better able to determine causal relationships between the identified semantic classes and semantic relationships.

The pharmacovigilance system 100 may also utilize the rules engine 250 of the server stack 210 to arrive at clinical inferences by applying one or more rules against a textual model. As an example, the server stack 210 may implement the rules engine 250 using Drools rules engine, which is a business rule management system (BRMS) that implements an enhanced implementation of a Rete algorithm for performing pattern matching. Drools is a commercially available rules engine. The Rete algorithm is a pattern matching algorithm that may be used to implement production rules system, but any suitable algorithm may be used. The rules engine may support grouping of individual rules or sets of rules, called rule agendas, and allow for selective firing of the rule agendas, or individual rules, which may result in improved system efficiency. The utilization of different occurrence models in application of the rule chains through the rules engine 250, as described in greater detail below, provides a unique advantage in processing natural language text when compared to traditional computer-based systems, and allows the pharmacovigilance system to arrive at deeper clinical insights than was previously possible. For example, different occurrence models may implicitly or explicitly define particular parameters (e.g., temporal parameters), and by placing the identified relationships within a particular occurrence model clinical inferences may be more readily identified.

One illustrative example of the general operation of the rules engine described by Drools literature, which is not intended to limit the inventions described herein, provides a simple rule to print out information about a holiday in July. It checks a condition on an instance of the Holiday class, and executes Java code if that condition is true.

```
rule "validate holiday"
dialect "mvel"
dialect "java"
when
    $h1:holiday( month == "july" )
then
    system.out.println ($h1.name + ":" + $h1.month);
end
```

According to the Drools literature, the purpose of dialect "mvel" is to point the Getter and Setters of the variables of the Plain Old Java Object (POJO) classes. Consider the above example, in which a Holiday class is used and inside the circular brackets (parentheses) "month" is used. So with the help dialect "mvel" the getter and setters of the variable "month" can be accessed. Dialect "java" is used to help write Java code in the rules. There is one restriction or characteristic on this. One cannot use Java code inside "when" part of the rule but Java code can be used in "then" part. One can also declare a Reference variable $h1 without the $ symbol. There is no restriction on this. The purpose of putting the $ symbol before the variable is to make the difference between variables of POJO classes and Rules The rules engine 250 may perform one or more medical inference tasks, including determining case admissibility and validity, categorizing medical conditions, categorizing drug reactions, determining case seriousness, determining if a reaction was expected, determining if a reaction was related and generating an appropriate reaction event signal. In performing the one or more medical inference tasks, the rules engine 250 may interface with the data virtualization and query engine 230, which may allow the rules engine 250 to access one or more databases 120, for example, the coding databases 123, the causal and temporal model databases 124, and curated drug safety and case databases 125. The rules engine 250 may analyze the structured natural language text generated by the NLP pipeline 220 to arrive at one or more clinical determinations.

The server stack 210 of the pharmacovigilance system 100 may also include a search framework 260, which may enable search capabilities for the pharmacovigilance system 100. As an example, the search framework 260 employed by the pharmacovigilance system 100 may be built on an open-source search software platform, such as for example, Apache Lucene search library, which is a Java-based indexing and search technology. The search framework 260 may facilitate searching different structured formats (e.g., XML/HTTP), and may provide higher order functionality, such as hit highlighting, search result caching, advance analysis and tokenization capabilities. As an example, the server stack 210 may implement Apache Solr search server, which is a high performance open source enterprise search server that operates on the Lucene core.

The pharmacovigilance system 100 may interface with the plurality of databases 120 through the data virtualization and query engine 230 of the server stack 210, which may allow the pharmacovigilance system 100 to access data from multiple heterogeneous data sources. The databases 120 may include the medical record databases 121, the curated reference and clinical knowledge databases 122, coding databases 123, causal and temporal model databases 124 as well as curated drug safety and case databases 125. Given the large amount of data contained in the databases 120, the data virtualization and query engine 230 may provide for rapid, model-driven, definition, integration, management and testing of data services. As an example, the server stack 210 may implement a data virtualization and query engine 230, for example, a Teiid data virtualization and query engine, which is an open source system and part of the JBoss Community of projects. Where the databases 120 share a common database model (e.g., a relational database), the data virtualization and query engine 230 may not be needed. However, where the different databases exist in different forms (e.g., relational databases, hierarchical databases, XML documents, flat files, or the like), the pharmacovigilance system 100 may utilize the data virtualization and query engine 230. Table 1, below, provides a non-exclusive list of databases which the pharmacovigilance system 100 may interface with and a description of the information that each database may contain.

TABLE 1

| Database | Description Usage |
|---|---|
| SNOMED-CT | SNOMED-CT provides clinical over 300,000 clinical concepts, identified by unique codes. The clinical concepts may cover medical diagnosis and therapies as well as well as medications, results and orders. |
| RX Norm | RxNorm provides information regarding clinical drugs including standard names and dosage information. It covers over 250,000 classes with 4.7 million relationship instances and over 79 relationship types. The information may include the drug code (ATC code) according to the Anatomical Therapeutic Chemical (ATC) Classification System, the brand name of the drug, the generic name for the drug, the active ingredient in the drug, the dosage forms that the drug may take, and the strength of a particular drug. |
| WHO-DD | World Health Organization Drug Database (WHO-DD) is a drug dictionary that contains drug information based on an international classification of medicines, designed by the WHO, that is monitored and managed by the Uppsala Monitoring Centre. It covers over 250,000 terms. |
| FMA | Foundational Model of Anatomy (FMA) provides a domain ontology representative of knowledge regarding the human anatomy, and contains approximately 75,000 classes and over 120,000 terms. The FMA additional contains over 2.1 million relationship instances corresponding to over 168 relationship types. |
| MEDDRA | MedDRA is a clinically validated medical terminology dictionary and thesaurus that used in the regulatory context, which provides adverse an adverse event classification system. The database has a 5 level hierarchical structure with 26 system organic classes at the top most layer, and over 71,000 terms at the lowest level. |
| Drug Bank | DrugBank provides bioinformatics and cheminformatics associating drugs with targets. The database contains 6825 drug entries, including 1541 FDA-approved small molecule drugs, 150 FDA-approved biotech drugs, 86 nutraceuticals, 5082 experimental drugs and 4323 non-redundant protein sequences. |
| EMC | The eMC provides unstructured safety label information, including drug indications, contraindications, known reactions and warnings regarding drugs marketed in the European Union. The eMC contains more than 9,000 documents that have been validated and approved by European governmental agencies responsible for drug licensing. |
| DailyMed | DailyMed provides safety label information for drugs marketed in the US, including information provided on FDA labels and package inserts. |
| FAERS | The FDA Adverse Event Report System (FAERS) contains over 7 million reports of adverse events experienced by patients consuming a drug, and reflects data going back to 1969. |

The medical record databases 121 may contain the medical information that is processed by the pharmacovigilance system 100. For example and without limitation, the medical information contained in the medical record databases 121 may include individual case safety reports for a patient 121*a*, medical literature relating to a patient population and/or drug 121*b*, regulatory warnings for a drug (e.g., FDA warnings) 121*c*, submissions made to patient self-reporting systems (e.g., MEDWATCH) 121*d*, or social and public data sources (e.g., WebMD, patientslikeme) 121*e*. The pharmacovigilance system 100 may maintain and update the medical record databases 121. Additionally or in the alternative, the medical record databases 121 may be updated and maintained by a separate organization where the data virtualization and query engine 230 allows the pharmacovigilance system 100 to interface and access the medical record databases 121.

The data virtualization and query engine 230 may be configured to detect the addition of one or more pieces of medical information into the medical record databases 121, which may automatically be processed, individually or in parallel, by the NLP pipeline 220 of the pharmacovigilance system 100. The medical information stored in the medical record databases 121 may arrive from different sources and may assume a variety of disparate formats. For example, the medical information may constitute individual medical records 121*a* that are structured in some way, for example, where the medical record 121*a* data is entered into a form or a template which a doctor or clinician has submitted. In other cases, the medical records may comprise unstructured data, for example, where the medical information is in the form of medical literature 121*b*.

The curated reference and clinical knowledge databases 122 may contain medical information, which may, for example and without limitation, be used by the NLP pipeline 220 in performing one or more natural language processing functions. For example, as described in greater detail below, the ontology framework 240 may access the curated reference and clinical knowledge databases 122 through the data virtualization and query engine 230 in building an ontology that the NLP pipeline 220 may apply in processing medical records 121*a*-121*e* contained in the medical record databases 121. The comprehensive nature of the curated reference and clinical knowledge databases 122 may provide for a robust ontology framework 240 that may help to identify numerous semantic classes and terms as well as numerous relationship types and instances.

By way of example, the NLP pipeline 220, in processing the medical records 121*a*-121*e* in the medical record databases 121, may use the information in the SNOMED-CT database to identify portions of the information that relate to medical conditions, procedures, and products. As another example, the NLP pipeline 220 may utilize the RX-Norm database to identify the one or more drugs being discussed in the medical records 121*a*-121*e*. Exploring this example further, a medical record 121*a*-121*e* may describe a patient's use of a drug by its brand name (e.g., Claritin). The NLP pipeline 220 may interface with the ontology framework 240, which in turn may draw upon the RX-Norm database through the data virtualization and query engine 230, to identify related terms or relationships. For example, the medical record 121*a*-121*e* may make reference to the same drug by a different name (e.g., its generic name, Loratidine, or its ATC code, R06AX13).

The causal and temporal model databases 124 may contain information indicating causal relationships or temporal relationships between a drug and an event experienced by the patient consuming the drug. The causal and temporal database 124 may be managed, for example, using OrientDB, which uses an object-oriented database where relationships are managed similar to that of a graph database having direct connections between records. The object-oriented databases support the use of iterators and enable graph-walking and span queries, which the pharmacovigilance system 100 may exploit to improve system performance. OrientDB is an open source database management system that may be available from Orient Technologies. Other database management tools exist (e.g., MongoDB and Couch DB), which may be adapted to perform a similar function. The NLP pipeline 220, through the data virtualization and query engine 230, may utilize the causal and temporal model database 124 in performing one or more of the natural language processing functions, for example, in performing temporal anchoring and ordering 227 or performing causal relationship identification 228. The NLP pipeline 220, for example, may identify causal and temporal relationships in the medical records 121*a*-121*e* that it is processing, which it may store in the causal and temporal model database 124. The NLP pipeline 220 may also be able to draw upon existing information in the causal and temporal model database 124 to identify the relationships present in the medical records 121*a*-121*e*.

The coding databases 123 (e.g., MedDRA and WHO-DD) may contain information regarding how certain drugs are classified, which may use one or more classification systems. The curated drug safety and case databases 125 (e.g., eMC, Daily Med, FAERS) may contain information regarding reactions experienced by patients consuming a drug, including, for example and without limitation, adverse event reactions, drug indications, contraindications, and possible interactions with other drugs. The rules engine 250 may apply rules to compare the relationships identified by the NLP pipeline 220 against those present in the curated drug safety and case databases 125, and in doing so the rules engine 250 may also draw upon information present in coding databases 123.

As mentioned above, the server stack 210 operating on the servers 110 of the pharmacovigilance system 100 may also provide an ontology framework 240, which may allow for the management of the ontology used by the pharmacovigilance system 100. As an example, the servers 110 may implement the Protégé ontology framework, which is a free, open source, ontology editor and knowledge acquisition system.

The different ontologies may be represented in the form of different semantic classes (e.g., medical condition and drug) and semantic relationships between these classes. A semantic class may also have one or more semantic subclasses (e.g., a drug dosage or rout of administration). The ontology may present the lexical ontology in terms of a symbolic class, which may be a higher-level abstraction of constituent class members. As for semantic relationships, the ontology may maintain associations between semantic classes and different predicates. For example, a patient condition relationship may connect the person semantic class (the symbolic class for a patient) with a medical condition semantic class, where the connection or relationship is identified based on the presence of additional predicate semantic classes.

The ontology framework 240 may utilize one or more base lexical ontologies 241 in addition to one or more custom ontologies 242, which may be associated with the pharmacovigilance system 100. A base lexical ontology 241 may, for example, provide a general lexical database for the English language, which may group English words into synonym sets, and record the various semantic relationships between these sets. For example, the ontology framework 240 may integrate WordNet, a freely available lexical database for the English language, as a base lexical ontology 241. As another example, the ontology framework 240 may integrate a Unified Medical Language System (UMLS) semantic network which provides a concise compilation of controlled vocabularies for use in the biomedical sciences. The UMLS semantic network provides over a million concepts and over five million concept names which are assigned to 135 semantic types and 54 semantic relationships. As noted, the ontology framework 240 may also facilitate the use and development of custom ontologies 242, which may provide the underpinnings for, or further enhance the effectiveness of, the pharmacovigilance system 100. Such custom ontologies 242 may be domain specific and tailored to identify particular issues of concern. A robust custom ontology 242, for example, may facilitate better semantic class identification and improved recognition of the complex relationships that may exist between the various semantic classes.

The custom ontology 242 may be constructed and updated in various manners. For example, the servers 110 of the pharmacovigilance system 100 may provide the ontology framework 240 with the information contained in the databases 120, which the ontology framework 240 may process to create an initial custom ontology 242. The servers 110 may also be configured to periodically scan the databases 120 to detect changes or additions to the databases 120, and may pass these changes along to the ontology framework 240 to augment the initial custom ontology 242. Given the size of the databases 120, the initial custom ontology 242 creation process may be relatively time consuming, though it need only be performed once. The ontology 240 framework may also allow for manual curation and versioning of the custom ontology 242 through an offline process. For example, the Protégé framework provides an interface allowing for the addition, deletion, or modification of the semantic classes and relationships within a custom ontology 242.

Additionally, or alternatively, the custom ontology 242 may be constructed as needed based on the processing of medical records 121a, 120b by the NLP pipeline 220. For example, when processing a medical record 121a, 120b the NLP pipeline 220 may identify a term not present in the base lexical ontology 241 or existing custom ontology 242. The NLP pipeline 220 may then query the data virtualization and query engine 230 for related terms. The NLP pipeline 220 or data virtualization and query engine 230 may communicate these results to the ontology framework 240, which may modify the custom ontology 242 accordingly.

As noted earlier, the pharmacovigilance system 100 may also provide an ITAP 270 to users of the system 100, which may make use of the server stack 210. The ITAP 270 may support various user roles, and may provide one or more ITAP interfaces 275 to the respective users. The ITAP 270 may operate using various java servlets and objects on the back end, which may, in turn, present ITAP interfaces 275 that utilize HTML5, JSP, widgets, or the like. For example, the ITAP 270 may provide an interface for advisory or case processors 276, an interface for safety and medical reviewers 277, and an interface for administrators, work managers, and information curators 278. Broadly speaking, the ITAP interfaces 275 may allow for interaction with the server stack 210 operating on the servers 110 in various manners and at various stages of information processing, which may serve to further enhance operation of the pharmacovigilance system 100.

The system administrator interface 278 may facilitate user management, allowing the administrator to control which users have access to the system 100. Work managers, likewise, may use the interface 278 in performing their responsibilities, which may include uploading cases into the system, assigning cases to case processor and medical reviewers, monitoring progress of the cases, and finally submitting the cases to the appropriate authorities. The work manager interface 278 may provide a dashboard providing an overview of the various cases which the manager oversees, and providing the state (e.g., unassigned, assigned, processing, ready for submission and submitted) of each case. The work manager interface 278 may allow the work manager to visualize this information in the form of charts and graphs, which the manager may be able to drill down into to obtain more particular case information. The work manager interface 278 may further allow for case tracking, allowing the manager to search for individual cases or groups of cases (e.g., by drug, location, or safety or medical reviewer) and providing visual indications as to changes in the case status. The interface 278 may also provide the manager with access to the case history, to see how the case is progressing. The work manager interface 278 may also allow the work manager to monitor the cases and workload of specific case processors and medical reviewers.

As noted earlier, the work manager interface 278 may allow the manager to upload case documents, which may be in a structured (e.g., CIOMS) or unstructured form. The work manager may also identify a case type when uploading the document, for example, spontaneous initial (where the case report indicates that an adverse drug event was experienced), spontaneous follow-up (where a request for follow-up was made by a medical reviewer) and clinical trial reports. Once uploaded, the cases may be automatically or manually assigned by the manager through the work manager interface 278. The work manager interface 278 may also be able to suggest safety reviewers and medical reviewers to whom the case may be assigned, for example, based on their work load or their specific skill set. The work manager may be able to dynamically re-assign cases through the work manager interface 278, to account for changing work conditions. Following case processing and medical review, the case may be ready for submission, and the work manager interface 278 may provide a listing of those cases to the manager for final authorization and submission. The work manager interface 278 may provide a status and action section, which may visually indicate completion of different steps in the process (e.g., case processing, medical review, etc.) and allow the manager to select the case for submission, for example, by clicking on a submit button or icon. Once cases have been uploaded and assigned, they may be presented as part of a dashboard provided in the safety and medical reviewer interfaces 277. Each case may be provided with a visual status indicator, showing the amount of progress that has been made or indicating the different stages of completion.

Figure 14:
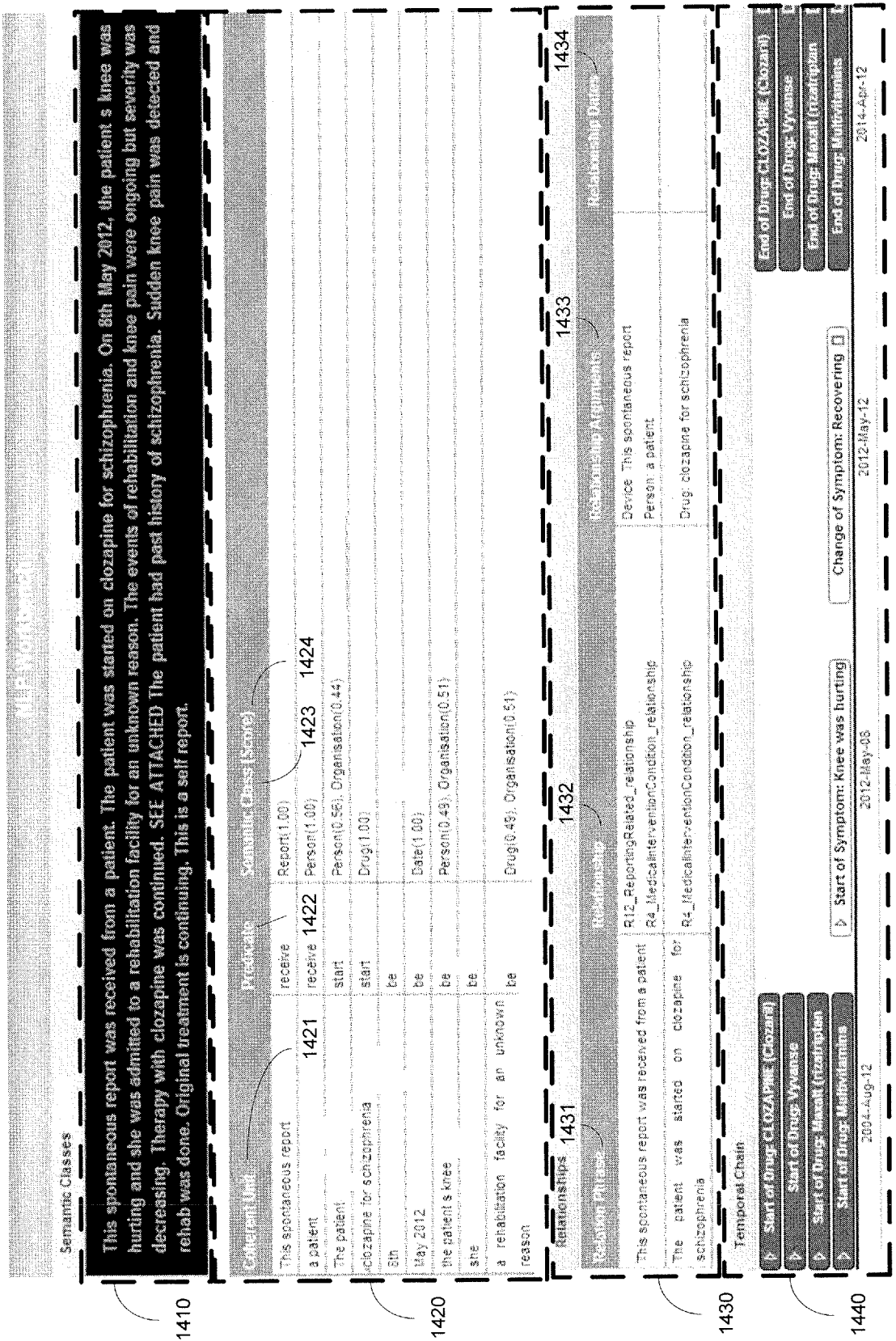
FIG. 14 provides a third example of an intelligent text analysis platform (ITAP) interface that the pharmacovigilance system may provide.

The ITAP interfaces 275 may also provide a feedback mechanism of sorts through which users of the pharmacovigilance system 100 may refine various elements of the pharmacovigilance system 100. At the case screening stage, for example, the medical reviewer interface 277 may display the sources document for the case, along with the relevant information extracted from the document, for example, the case information, patient details, source details, drug details and event details. The medical reviewer may be able to correct and validate this information through the interface 277. For example, the ITAP interfaces 275 may allow a user to identify one or more members of a semantic class, which the ontology framework 240 may store and use in subsequent processing. For example, the medical reviewer in processing the case may medically code the drugs that the patient is taking, and may be provided with an integrated search tool that may draw upon the drug coding database 123. The ITAP interfaces 275 may similarly allow a user to identify relationships between different semantic classes, which the ontology framework 240 may also store and use in subsequent processing. For example, the medical reviewer may verify that the identified event details are accurate. Where available, the interface 275 may also provide information about the patient history including any pre-existing conditions, and may prominently place this information in the interface 275 or provide some other visual enhancement allowing the medical reviewer to readily observe the information. The ITAP interfaces 275 may facilitate this process by providing a graphical or interactive interface to the users that may simplify the process. With reference to FIG. 14, for example, the ITAP interface 275 may present the textual content being processed 1410 and may provide tools for semantic class identification 1420, semantic relationship identification 1430, and temporal chain creation 1440.

Regarding the semantic class identification tool 1420, the ITAP interface 275 may present a listing of the identified semantic classes, for example, by listing the constituent coherent units 1421 along with an associated verb predicate 1422, as well as the identified semantic class 1423 and semantic class score 1424. Likewise, regarding the semantic relationship identification tool 1430, the ITAP interface 275 may present a listing of the identified semantic relationships, for example, by listing the relationship phrase 1431 in question and the identified relationship(s) 1432, along with the corresponding relationship arguments 1433 and relationship dates 1434.

The ITAP interfaces 275 may also present a graphical overlay that may allow the user to associate certain words with a semantic class by "clicking" on the term and specifying the semantic class, for example, through a drop down list or text field. The ITAP interface 275 may similarly allow the user to identify one or more relationships in a given phrase. The ITAP interfaces 275 may further suggest known relationships that the user may select from, or allow the user to define a new relationship. For example, a user of the ITAP interfaces 275 may identify a relationship between two particular members of a semantic class, which the ontology framework 240 may then apply to the semantic class as a whole based on the deductive classifiers.

Figure 10:
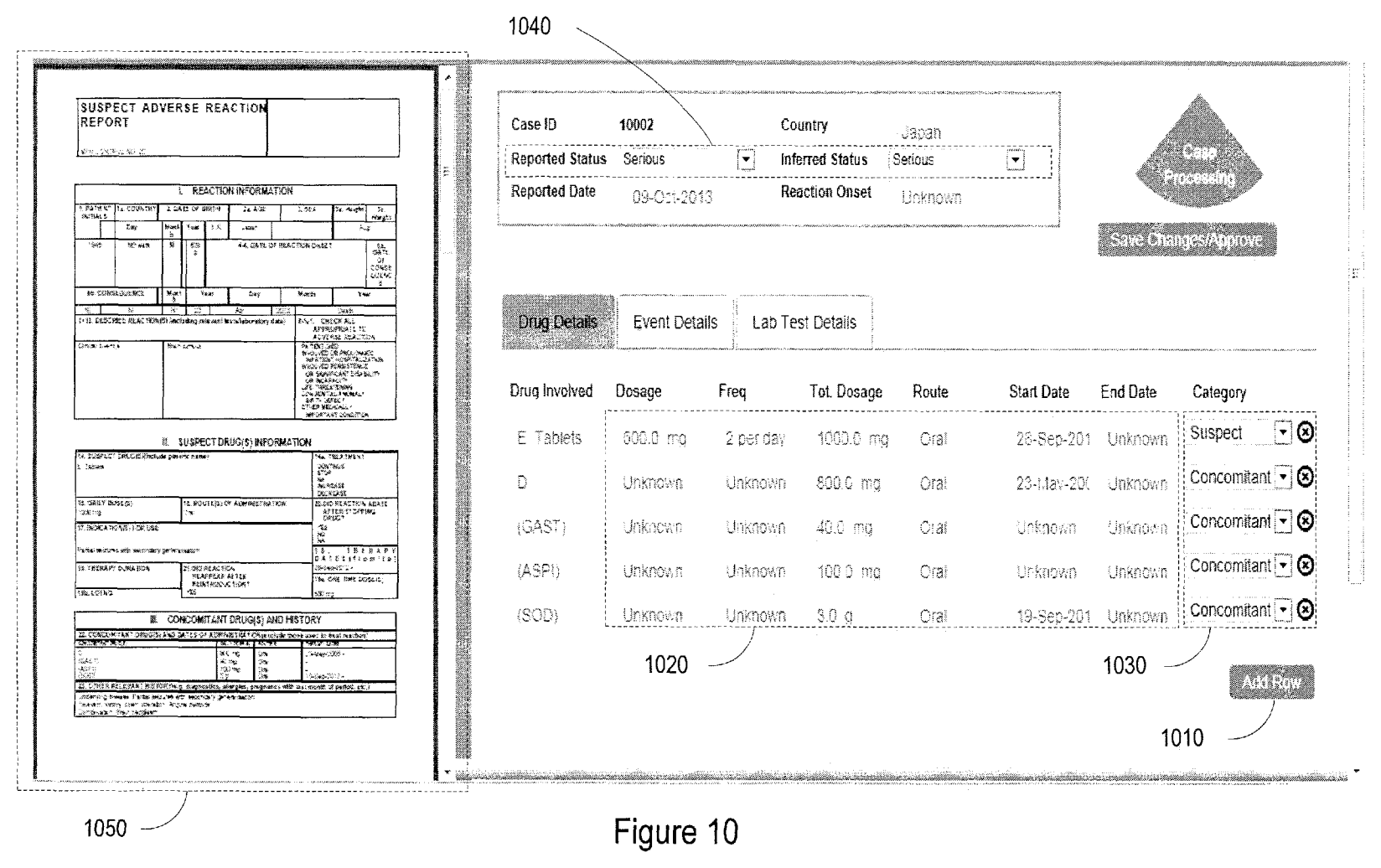
Figure 11:
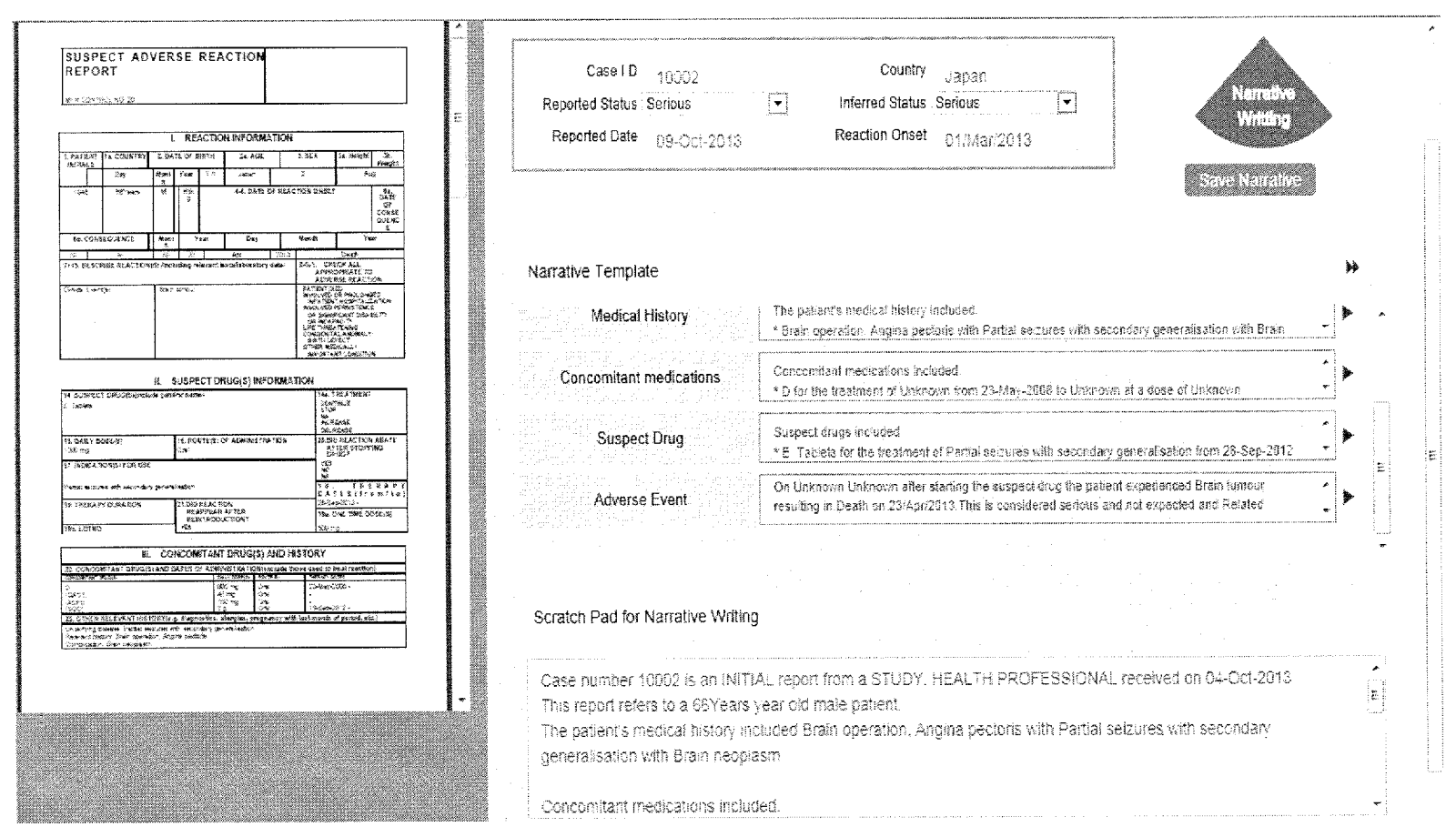

Regarding the temporal chain creation tool 1440, the ITAP interface 275 may present a listing of identified temporal events 1441, which may be arranged in chronological order. As illustrated in FIG. 14, for example, the temporal chain creation tool 1440 may identify when a patient started taking a drug and when the patient stopped taking the drug along with when the patient started exhibiting symptoms and if and when the symptoms changed. The ITAP interface 275 may allow the user to modify identified events, add additional events and adjust the event timeline, as well as allowing the user to link or associate different events with one another. In other instances, for example based on the role of the user or the interface on which it is being presented, the system may present the identified temporal chains in a "read only" mode, in which modification of the temporal chains is disabled. Furthermore, with reference to FIGS. 10 and 11, the ITAP interfaces 275 may allow users to adjust, enter, and validate clinical or medical inferences extracted by the pharmacovigilance system 100. In FIG. 10, for example, a user of the ITAP interface 275 may be able to verify the different semantic classes and relationships that were automatically identified by the pharmacovigilance system 100. For example, a user may manually add information 1010, and enter attributes that were previously unknown or modify entries populated by the system 1020. The user, who may have clinical experience, may be able to adjust the inferred status of the case 1040 or the categorization of a drug (e.g., suspect, secondary suspect, concomitant, etc.) 1030. In facilitating this process, the ITAP interface may also integrate the original source document 1050 for the user to review. The pharmacovigilance system 100 may also highlight the information in the original source document 1050 that was used to populate the entries in 1020 or support the inferences presented 1030, 1040. Similarly, FIG. 11 illustrates an ITAP interface 275, allowing the user to modify the narrative that was generated by the pharmacovigilance system 100.

The ITAP interfaces 275 may also provide an NLP workbench, that may be quickly accessed through the interface 275 and may present the annotated text, identified entities and relationships, along with chronological and causal ordering of different events. The annotated text section may display the free form text processed from the document, highlighting different identified semantic classes (e.g., person, drug, medical condition) which may be distinguished based on a highlighting color, for which a legend may be provided. The workbench may also provide a listing of the different entities present in the text, where the entities are arranged and grouped based on the ontology framework 240, and the user is able to drill down into particular groups through the ITAP interface 275. Similarly, the interface 275 may provide a listing of identified relationships allowing the user to drill down in to the details of particular relationships, providing additional details regarding how the different relationship elements are satisfied.

The ITAP interface may also arrange and present the different identified event chains in a chronological order, where an event chain having no identified date is labeled as 'unknown', and may be arranged based on its occurrence within the case document. Similarly, causal chains may be presented through the interfaces 275, where the user is able to drill down on particular causal chains. By way of example, the interface 275 may provide a reporting chain, that shows the data pertaining to case reporting, a etiology chain, displaying important events from the case document based on order of occurrence (e.g., patient history followed by indication, intervention, reaction, treatment and outcome), a hospitalization chain displaying information with respect to hospitalization, an intervention chain displaying the drugs taken by the patient, and a clinical drug trial chain, used for clinical drug trials.

In addition to the NLP workbench, the ITAP interfaces may provide a rules dashboard, which may provide a dynamically update status regarding one or more rules, for example, those rules relating to a case admissibility, case seriousness, case outcome, suspected drug indication relatedness, suspect drug adverse event expectedness and suspect drug adverse event relatedness. The rules dashboard may provide a visual indicator for each of these rules allowing different users to quickly assess the different medical inferences which they may represent. This information may be used, for example, by the work manager to determine if the case is ready for submission.

Users of the pharmacovigilance system 100 may also help to define and modify ontologies through the various ITAP interfaces 275, which may facilitate interaction, through the ontology framework 240, with one or more ontology models 241, 242. For example, the ontology framework 240 may provide visualization support for the pharmacovigilance system 100, which may present ITAP interfaces 275 to users of the system 100 allowing them to manipulate one or more ontology models. The ontology framework 240 may also provide for and utilize deductive classifiers, which may serve to validate ontology models for consistency and may be used to infer new information based on an analysis of the ontology. Further description of the pharmacovigilance system 100 will be provided with reference to FIGS. 3-7, which illustrate, at a high level, how an exemplary pharmacovigilance system 100 may operate.

The pharmacovigilance system 100 may pass input documents 301 from disparate sources containing structured or unstructured text 302, through an input canonizer 303, which may arrange the text 302 using a canonical format template 304 (e.g., XML template) to form data in a canonical format 305 by parsing the text 302 in the input documents 301 and dividing the text into different segments (e.g., sentences, phrases or clauses) (401). As an example, the data virtualization and query engine 230, may provide medical records 121*a*-121*e* from the medical record databases 121. The medical records 121*a*-121*e* may contain documents that use the Portable Document Format (PDF), which may be passed through the input canonizer 303 to form an Extensible Markup Language (XML) file 305 by parsing the textual data and placing the identified segments into an XML template 304. The extraction and canonicalization of input documents helps to fuse structured and unstructured data from different sections of various safety forms (e.g., CIOMS) into pre-defined elements, and allows the system to better handle improperly identified inputs, for example, those which may result from inaccurate optical character recognition or similar techniques for extracting information from document images. The canonical input XML also facilitates processing by the NLP pipeline 220 as it does not have to deal with multiple structural formats, or free form running text.

The data in canonical format 304 may be passed to the NLP pipeline 220, which may perform various information extraction tasks, including semantic class identification and instantiation (402*a*). A semantic class may also have subclasses, which the NLP pipeline 220 may be enabled to identify and extract. By way of example, with reference to FIG. 5, The NLP pipeline 220 may identify different semantic classes, including a patient semantic class 501, an adverse reaction semantic class 502, a predicate semantic class 503, a drug semantic class 504, an indication semantic class 505 and a drug dosage semantic class 506.

Table 2, below, provides additional examples of some of the semantic classes which may be extracted from the text by the NLP pipeline 220. A semantic class may have different types and take different forms and may be associated with an individual term or a group of terms. A semantic class, broadly speaking, represents a particular concept, where the symbolic form of the semantic class is a set of lexical tokens (which may be a word, a part of a word, or a group of words). The lexical tokens belonging to a semantic class may capture the concept fully, partially, or by providing linguistic clues in the form of suffixes, prefixes, and infixes. By way of example, the term "disease" would completely describe a lexical member of the medical condition symbolic class. Likewise, the term "psychosomatic" could partially describe a semantic class and may serve as a 'key term', where the linguistic clues are provided by certain 'key term patterns', for example where a prefix (e.g., 'hypo$') or suffix ('$phillia') is present. As noted above a semantic class may have one or more subclasses, which may be seen as attributes of the superclass. For example, terms belonging to the symbolic age semantic class may also be attributes of the symbolic person semantic superclass, which may carry with it its own set of associations (e.g., the symbolic nationality class may be associated with a symbolic organization semantic class).

As described in greater detail below, semantic classes may be identified in text through the presence of its symbolic class term, where the pharmacovigilance system 100 may take into account the linguistic (or lexical), semantic, morphological and contextual mapping of the text. With regards to the linguistic mapping, the pharmacovigilance system 100 may parse the text to match terms against symbolic classes in the lexical ontology. The pharmacovigilance system 100 may calculate the nearness of a lexical match using the Jaro-winkler lexical scoring algorithm which produces a score of between 0.0 and 1.0, and may provide a match weight of 1.0 for lexical tokens that are complete matches, and match weights of 0.5 for partial matches (i.e., key terms and key term patterns). By way of example, the tokenizer may identify "mouth ulcer" comprising the individual terms "mouth" and "ulcer". The "mouth" term may be directly matched against a term present within the anatomy semantic class described within the ontology framework, producing, for example, a linguistic matching score of 1.0 (on a 0.0-1.0 scale). The system may similarly match the term "ulcer" directly to the medical condition semantic class within the ontology framework, likewise, producing a linguistic matching score of 1.0.

In a bit more detail, the pharmacovigilance system 100, for a particular token returned by the NLP pipeline 220, may calculate a matching score for a semantic class. For instance, the term "mouth ulcer" may produce a matching score for the anatomy semantic class of 0.5, which itself may be an average or weighted average of the linguistic matching score for the constituent terms. Continuing the previous example, the term "mouth" may produce a linguistic matching score of 1.0 with the anatomy semantic class (based on a direct match) and the term "ulcer" may produce a linguistic matching score of 0.0 with the anatomy semantic class (as it is unrelated), resulting in a weighted average of 0.5 (or (1.0+0.0)/2). The pharmacovigilance system 100 may similarly calculate a matching score for the medical condition semantic class. For example, assuming that the term "ulcer" is not a direct match, the system may produce a matching score of 0.425 for the medical condition semantic class, with "mouth" having a linguistic matching score of 0.0 against the medical condition semantic class and "ulcer" having a linguistic matching score of 0.85 (calculated using the Lin methodology).

Although the token "mouth ulcer" may have a greater matching score with the anatomy semantic class relative to the medical condition semantic class (0.5>0.425), it may be the case that the ontology framework 240 has defined a rule, logic, or relationship in which the medical condition semantic class is seen as subsuming (or acting as a superclass for) the anatomy semantic class. For example, the token "left ear" may be a partial attribute, or subclass, of the anatomy semantic class. Where a subsuming rule exists, the pharmacovigilance system 100 may attribute the token with, or attach the token to, the superclass. Returning to the previous example, the pharmacovigilance system 100 may attribute "mouth ulcer" to the medical condition semantic class despite having a greater matching score with the anatomy semantic class, given that the medical condition semantic class subsumes an anatomy subclass.

The pharmacovigilance system 100 in performing linguistic matching may also determine a linguistic matching score for certain descriptive terms, or key terms. For example, the system may identify the key terms "pruritus" or "aggravated" and may return a linguistic matching score of 0.5 for each. The key term may also be part of a larger token, for example "pruritus wound", which may have a corresponding matching score of 0.75 (or (0.5+1.0)/2) for the medical condition semantic class, with "pruritus" being given a weight of 0.5 (based on identification as a key term) and "wound" being given a weight of 1.0 (based on a direct match). The pharmacovigilance system 100 may identify key terms directly or based on a prefix, suffix, or other matching pattern. For example, the system may identify the term "hypochondria" as a key term that matches the pattern "hypo$" (the '$' symbol being a wildcard of unknown length), and may be given a score of 0.5.

The pharmacovigilance system 100 when parsing the text may also look at the semantic mapping of the text to perform information theoretic matching, and may calculate the nearness, or distance, of the term, for example, using the Lin semantic scoring method. The pharmacovigilance system 100 may also calculate the contextual match in similar fashion by evaluating the neighborhood of a term, where the contextual score of a term is adjusted based on its likelihood to engage in a semantic relationship with another semantic class, which may be previously identified. As for the morphological mapping, the pharmacovigilance system 100 may look at the part-of-speech pattern of the lexical token or term, or identify a numerical value, and may determine whether the term has a similar part of speech pattern as a candidate symbolic semantic class. For example, for the age or weight semantic class, the pharmacovigilance system 100 may look for a pattern of <#, noun>. The pharmacovigilance system 100 may have a morphological matching score of 1.0 for both the token '23 years' and '63 kilograms'. In this example, the pharmacovigilance system 100 may use the lexical or semantic matching score to disambiguate the token to either the age or weight semantic classes.

More broadly, the pharmacovigilance system 100 may combine the lexical, semantic, contextual and morphological scores to form an aggregate score, where the maximum score is selected for potential assignment to a semantic class. The scores may be added to one another and may be normalized in some way. The pharmacovigilance system 100 may also apply a hierarchical or sequential approach in aggregating the scores. For example, if the pharmacovigilance system 100 determines a lexical score above a certain threshold (e.g., 0.85 or 1.0) it may not be necessary to continue to determine the semantic, contextual, and morphological scores. Additionally, if the lexical score falls below the threshold, the pharmacovigilance system 100 may adjust the lexical score or reject it entirely, for example, by setting its value to 0.0, as lexical scoring alone may be susceptible to misidentification. By way of example, the term 'cold' and 'old' may have relatively similar lexical scores but have different semantic meaning. By adjusting or rejecting the lexical score in those situations where a strong (i.e., above the threshold) match may not be present, the pharmacovigilance system 100 may place greater weight on the semantic, contextual and morphological scores and in this way may be able to more accurately classify the term.

It may also be the case that the lexical, semantic, contextual and morphological analysis and scoring is insufficient to accurately classify a token or term. This may be based on a minimum threshold, for example, where the aggregate matching score is greater than 0.7. The pharmacovigilance system 100 may also look at the distribution of scores in a relative sense, for example, requiring the highest score to be 40% greater than the next highest score. For instance, the term 'paracetamol' may have a score of 0.6 with the drug semantic class, 0.4 with the medical condition semantic class, and 0.5 with a medical procedure semantic class. In order to ensure accurate classification, the pharmacovigilance system 100 may send the potential semantic class for disambiguation against the databases 120, for example, the clinical knowledge databases 122, where the pharmacovigilance system 100 may vote to approve of the class selection and may proceed with assigning the term to the potential semantic class. Continuing with the previous example, the pharmacovigilance system 100 would query the databases 120 to determine if the term 'paracetamol' is present in a particular database, and may then assign the term to the drug semantic class. If the term is rejected (i.e., it is not present in the databases 120), the potential semantic class having the next highest aggregate score may be selected for disambiguation and database confirmation. Disambiguation of terms based on database queries may itself result in misclassification of terms. For example, the term 'malaria' while a common medical condition may also be a drug, and when the term 'malaria' is disambiguated it may be misidentified as a drug. To avoid repeating such errors, users of the pharmacovigilance system 100 may be able to add commonly misidentified terms to a database query stop-list.

TABLE 2

| Semantic Class | Brief Description | Operational Parameters |
| --- | --- | --- |
| Anatomy | This class may identify different bodily structures. | The class may have different types, for example, BodyPart and BodyLocation. |
| Date & Time | This class may identify date and time concepts. | The class may take different forms (e.g., absolute or relative) and have different types. |
| Device | This class may identify different medical devices. | The class may take different forms and have different sub-classes, for example, identifying the type of device and the device manufacturer. |
| Drug | This class may identify information related to drugs that may be consumed by a patient. | The class may take different types, including, e.g., suspect drug, concomitant drug, or treatment drug. The class may take different forms including, e.g., brand, generic, ATC. The class may also have different sub-classes, e.g., constituent ingredients, method or route of administration (e.g., oral or injection), dosage form, and drug manufacturer. |

TABLE 2-continued

| Semantic Class | Brief Description | Operational Parameters |
|---|---|---|
| Identifier | This class may be used to capture a unique identifier. | |
| Lab Test | This class may identify lab test related information. | |
| Medical Condition | This class may identify different medical conditions. | |
| Organization | This class may identify different organization names. | The class may have different types, e.g., hospital, affiliate, partner, manufacturer. |
| Patient Vitals | This class may identify different vital conditions for a patient. | The class may take different forms and may have different sub-classes, including, e.g., height, weight, blood pressure. |
| Person | This class may identify a person or a patient. | The class may include patient, practitioner (doctor, nurse, professional, reporter), and may include different sub-classes, including, e.g., age and ethnicity. |
| Procedure | This class may identify different medical procedures. | The class may take different types, including, e.g., a therapeutic procedure or a diagnostic procedure. |
| Report | This class may identify the type of report being considered. | The class may take different types, including, e.g., a spontaneous patient report, or a clinical study. |

The NLP pipeline 220 may also identify semantic relationships, for example, whether a patient has a disease 511 or whether a patient is undergoing therapy or treatment 510. The NLP pipeline 220 may, for example, attribute these relationships to a sentence or phrase in the text being processed. Table 3, below, provides examples of the semantic relationships which may be identified by the NLP pipeline 220. The table also provides examples of the meta-structure or patterns that the NLP pipeline 220 match the text against in order to identify the presence of a relationship. By way of example, with reference to relationship R2 below, the pharmacovigilance system 100 may look for a patient semantic class, an organization semantic class, and a predicate semantic class (i.e., "hospitalize|admit|discharge|transfer|refer|vacate") that may indicate a physical event relationship.

TABLE 3

| Relationship Type | Meta-structure/Pattern | Relationship Type |
|---|---|---|
| R1 | [procedure] [show \| reveal \| detect \| indicate \| confirm \| establish \| produce \| observe \| diagnose \| prove \| disprove \| conclude \| exclude] [medical condition] | The matching pattern may identify relationships between diagnostic procedures and medical condition. |
| R2 | [patient] [hospitalize \| admit \| discharge \| transfer \| refer \| vacate] [organization] | The matching pattern may identify physical event relationships. |
| R3 | [procedure \| device] [perform \| do \| insert \| withdraw \| conduct \| undergo] [anatomy] [medical condition] | The matching pattern may identify relationships between intervention procedures and medical conditions. |
| R4 | [drug \| procedure] [prescribe \| advise \| give \| do \| take \| administer \| recommend \| receive \| issue \| continue \| discontinue \| withdraw \| start \| stop \| increase \| decrease \| restart \| rechallenge \| dechallenge] [medical condition \| patient] | The matching pattern may identify medication intervention relationships. |
| R5 | [medical condition] [associated with \| exhibited in \| show \| indicate \| include \| contain] [medical condition] | The matching pattern may identify relationships between two medical conditions. |
| R6 | [drug \| procedure] [cause \| result in \| lead to \| relate to \| associated with] [medical condition] | The matching pattern may identify relationships between a drug and a reaction. |
| R7 | [drug \| procedure] [prescribe \| advise \| give for \| receive \| take for \| administer] [medical condition] | The matching pattern may identify relationships between a drug and a condition. |
| R8 | [medical condition] [precede \| follow \| co-occur \| co-exist \| also has \| co-present] [medical condition] | The matching pattern may identify comorbidity relationships. |
| R9 | [patient vitals] [indicate \| suggest \| suspect] [medical condition] | The matching pattern may identify relationships between patient vitals and medical conditions. |
| R10 | [lab tests] [show \| reveal \| detect \| indicate \| confirm \| establish \| produce \| diagnose \| prove \| disprove \| conclude \| exclude \| measure] [medical condition \| patient vital] | The matching pattern may identify relationships between clinical tests and medical conditions. |

TABLE 3-continued

| Relationship Type | Meta-structure/Pattern | Relationship Type |
|---|---|---|
| R11 | [medical condition] [spatially related to (find \| see \| locate near \| adjacent to \| surround)] [anatomy] | The matching pattern may identify a relationship between a medical condition and anatomy. |
| R12 | [report \| lab tests] [create \| submit \| generate \| receive \| receive via \| obtain] [organization \| reporter] | The matching pattern may identify a documentation relationship. |
| R13 | [patient] [experience \| is \| feel \| has \| suffer \| present with \| suspect \| exacerbate \| aggravate \| recur \| reappear \| disappear \| subside \| has outcome] [medical condition] | The matching pattern may identify a relationship between a patient and a condition. |
| R14 | [patient] [had \| experienced in past \| history of \| underwent \| was \| had anomaly] [medical condition \| procedure] | The matching pattern may identify a relationship between a patient and a medical history. |
| R15 | [drug \| procedure] [has \| administer \| treat \| prescribe \| recommend] [dosage] | The matching pattern may identify a relationship between a drug and a dosage form. |
| R16 | [concept] [is \| has \| concern \| contain \| describe \| type of] [sub-class \| attributes] | The matching pattern may identify a relationship between a semantic class and an attribute of the class. |
| Seriousness | [reporter] [assesses \| confirms \| tells \| reports] [serious] | The matching pattern may identify a relationship reflecting a serious reported case, where [serious] may also be matched to similar terms. |
| Causality | [reporter] [drug \| procedure] [cause \| result in \| lead to \| relate to \| associated with] [medical condition] | The matching pattern may identify a reported causality case, where the pattern of R6 is accompanied by the [reporter] semantic class. |

The NLP pipeline 220 may also identify optional parameters that may correspond to an identified relationship. The optional parameters may include a severity or degree parameter, a certainty parameter, a course parameter, a status or state parameter, discourse parameter and temporal parameter.

The severity or degree parameter identified by the NLP pipeline 220 may refer to terms that indicate the severity of a medical condition, and may optionally be associated with the medical condition. The severity and degree parameter may, for example, classify terms as mild, moderate or acute. The severity and degree parameters may be retrieved from one or more databases 120 (e.g., SNOMED-CT or Mayo Clinic) through the data virtualization and query engine 230.

The certainty parameter identified by the NLP pipeline 220 may refer to terms indicative of an epistemic modality, which may cover certainty, speculation and judgment. The certainty parameters may have an associated polarity. For example, terms may have a positive polarity (e.g., is, has, confirm, establish, produce, prove). Other terms may have a speculative or judgmental polarity (e.g., might, probably, tentatively), which the NLP pipeline 220 may identify through the use of auxiliary phrases, adverbs and adjectives. Some terms may be associated with a negative polarity, which may be identified as antonyms of the positive polarity terms or as negation operators (i.e., not or opposite).

The course parameter identified by the NLP pipeline 220 may be associated with the nature of the medical condition or treatment (e.g., seasonal, chronic, gradual onset, acute onset, benign course). The parameter may be divisible into three broad categories, referring to terms that are benign to moderate (e.g., gradual, benign, non-recurrent), acute (e.g., sudden onset, brittle, aggressive), or cyclical and long-running (e.g., chronic, long-term, recurrent).

The status or state parameter may be associated with terms that modify the medical condition and may denote the status of the condition (e.g., low, high, enlarged, restricted) or one of the outcomes (e.g., resolved, unresolved, fatal). The medical condition status parameter may refer to positive states where the status has improved with respect to a previous state or negative states where the status has deteriorated or failed to improve with respect to the previous state.

The discourse parameter identified by the NLP pipeline 220 may be used to identify terms that establish a linguistic or textual causality and temporality of a sentence, or relationship, relative to another sentence, or relationship. For example, the discourse parameter may refer to forward positive causal terms (e.g., hence, consequently therefore) backward positive causal terms (e.g., because, due to, as), forward negative discourse terms (e.g., but, however, yet), and backward negative causal discourse (e.g., although, notwithstanding, even though). With respect to temporality, the discourse parameter may, for example, refer forward temporal or conjunctive terms (e.g., later, afterwards, next) or backward temporal or conjunctive terms (e.g., before, previously earlier). The discourse parameter may also identify conditional terms (e.g., unless, until, based upon, assuming that).

The NLP pipeline 220 may also determine temporal parameters or operators, which may be obtained from terms identified as being within the date and time semantic class. The temporal operator may refer to an absolute date or time (e.g., $9^{th}$ of March or 2014-03-09), a relative date or time (e.g., "three days later" or "a few hours earlier"), a referential date or time (e.g., "at the time of discharge" or "during the last operation") or a time span (e.g., "since childhood" or "for the past 2 years"). Temporal operators for absolute date and time may be determined by looking at terms identified as falling within the date and time semantic class. Similarly, temporal operators for relative dates or times, referential dates or times and time spans may be determined by looking at terms identified as discourse parameters.

The pharmacovigilance system 100 may place an identified relationship within an occurrence model, which may have an associated temporal parameter that may be explicitly or implicitly defined. The relationships may be classified as an external physical occurrence, a case document related occurrence, a medical diagnostic or finding occurrence, a medication intervention occurrence, an indication occurrence, a medical state occurrence, a medical history or co-morbidity occurrence, or a dosage occurrence.

An external physical occurrence may cover relationships (e.g., R2) that depict external medical activities (e.g., admission, transfer, discharge, or re-admission). A case document related occurrence may cover relationships (e.g., R12) in which the document being processed is identified as clinical documentation (e.g., report generation, update or follow-up). A medical diagnostic or finding occurrence may cover relationships (e.g., R1, R9, R10) that positively or negatively confirm the presence of a medical condition. A medication intervention occurrence may cover relationships (e.g., R4) identifying an event that is associated with an external medical stimulus that may have been given to the patient. An indication occurrence may cover relationships (e.g., R3, R7) that identify the medical indication or reason for which a drug was given or for which a procedure was performed. A medical stat occurrence may cover relationships (e.g., R13) that represent the current medical state or condition of a patient. The medical history and co-morbidity occurrences may cover relationships (e.g., R8, R14) that reflect prior conditions in the patient's medical history or co-morbidity conditions for the patient. A dosage occurrence may cover relationships (e.g., R15) that describe the dosage of a drug taken by the patient or a therapy or type of procedure given to or performed on the patient, respectively.

In addition to performing semantic class and relationship identification (402a), the pharmacovigilance system 100 may process the data to create a causal and temporal semantic model of the text, which may allow the pharmacovigilance system 100 to arrange the text in temporal order (402b).

The causal temporal model formed by the pharmacovigilance system 100 may depend on the occurrence model of the relationship. For example, in a report occurrence model, the model may be centered on a report receipt date, where the identified elements may relate to case processing. The pharmacovigilance system 100 may determine if identified elements fall within a pre-report temporal period (e.g., past medical history) or a post-report temporal period (e.g., follow-up information, lab test reports, doctor's narrative). As another example, the identified relationships may correspond to a medical occurrence model where the model is centered around a reaction onset date, and the identified elements may relate to medical events happening in the case. Some elements may pre-date the reaction onset date (e.g., medical history, or the administration of a suspect drug), while other elements may correspond to a treatment narrative for the reaction (e.g., treatment drug given, suspect drug de-challenged/re-challenged/stopped, medical condition observations), which may terminate in the ultimate case outcome (e.g., recovery or fatality).

Figure 6:
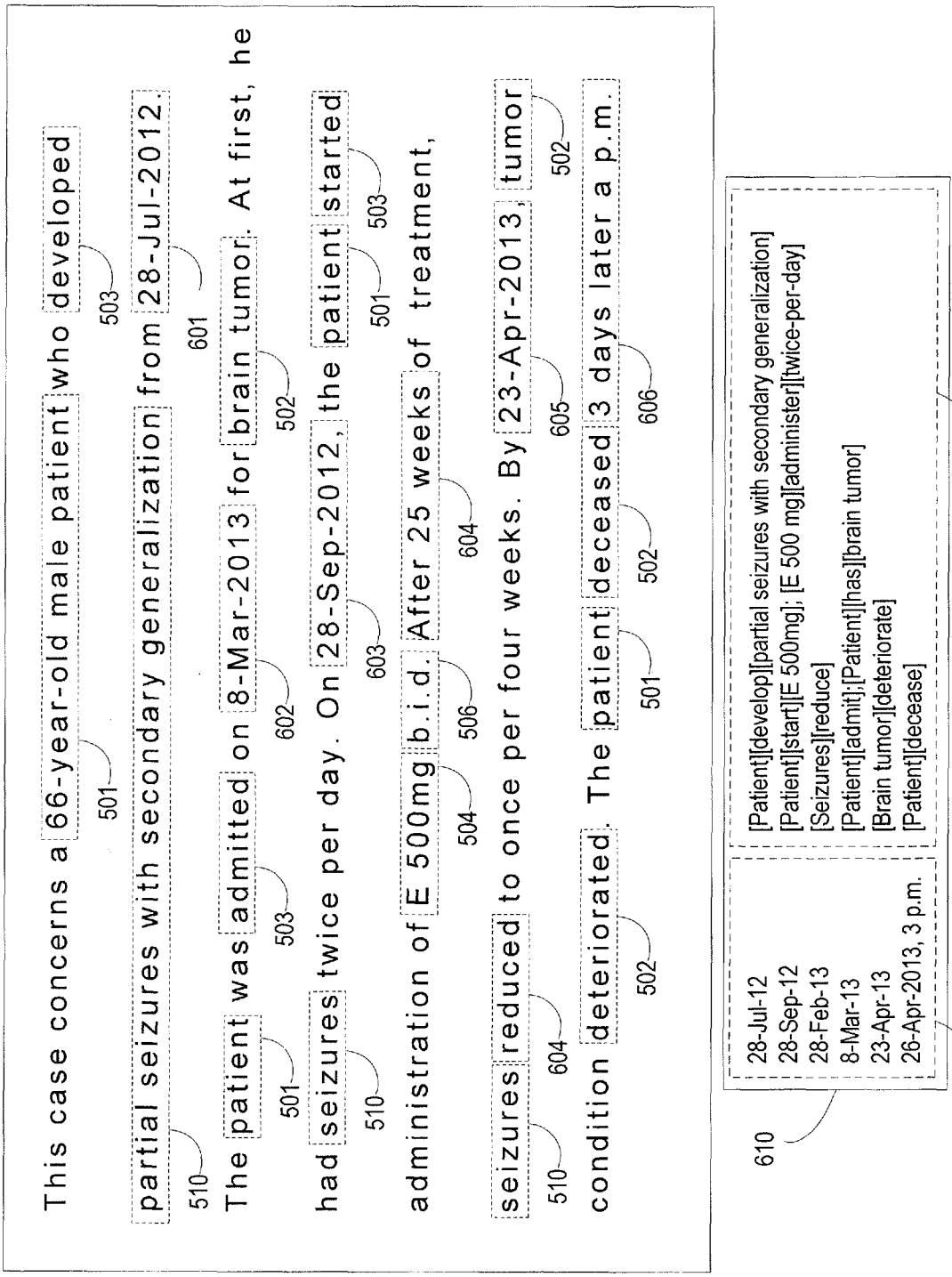
FIG. 6 illustrates an example of the temporal ordering that may be performed by the pharmacovigilance system.

With reference to FIG. 6, a medical occurrence model is illustrated. The pharmacovigilance system 100 may identify temporal elements corresponding to the occurrence of a reaction event 601, a medical observation event 602, a drug treatment event 603, a medical observation event 604, a medical observation event 605, and a case outcome event 606. The pharmacovigilance system 100 may then form a temporally ordered list 610 of the relationships identified in the document, which may involve ordering matching relationship occurrences 630 based on the explicit or implicit determination of temporal parameters 620.

The pharmacovigilance system 100 may also identify the presence of possible causal chains for relationships between a suspect drug and an observed reaction. The pharmacovigilance system 100 may use temporal discourse markers to draw associations between an ordered list of relationships, which, in some instances, may be limited to a subset of identified relationships. For example, the pharmacovigilance system 100 may selectively examine relationships between a patient, a medical condition, a suspect drug or treatment, and an adverse reaction (e.g., R4, R5, R6, R7, R11, R12, R13, R15, Causality). With reference to FIG. 7, for example, the pharmacovigilance system 100 may look at relationships involving a patient 701, an existing medical condition 702, suspect drugs and treatments 703, and adverse reactions 704. The pharmacovigilance system 100 may use the temporal discourse markers 705 to infer potential causal chains 710, which may be further evaluated by the pharmacovigilance system 100.

The following description provides an example of a method of implementing the above described logic to form causal and temporal models from unlabeled text.

The pharmacovigilance system 100 may begin by identifying semantic classes from unlabeled data. This may involve processing the unlabeled data to form various 'chunks' of text, for example, using the NLP pipeline 220, and matching the coherent chunk units to a semantic class (e.g., the semantic classes identified in Table 2). The NLP pipeline 220 may utilize machine learning code that is trained to detect the boundaries of words or groups of words, so that the combination of words having the highest probability of occurring together (in a linguistic sense) are grouped together as a coherent 'chunk'. In situations where the semantic class has certain attributes or sub-classes, the pharmacovigilance system 100 may also attempt to fill, or match, these attributes. If no match is found for an attribute, the pharmacovigilance system 100 may specify a 'null' or 'UNKNOWN' value. The matching process may, for example and without limitation, look at part-of-speech tags, lexical similarities between the chunks and a set of 'seed words' which correspond to a semantic class, and other syntactic patterns and may determine a matching score for each chunk. Where the score is below a threshold value, the pharmacovigilance system 100 may determine that the chunk cannot be disambiguated and may present the chunk to the user for identification and disambiguation.

Once matching is complete and the semantic classes have been identified, the pharmacovigilance system 100 may proceed with sentence simplification, which may involve breaking compounds sentences based on constituent conjunctions or punctuation markers. The pharmacovigilance system 100 may then process each simple sentence (i.e., with one primary predicate) and identify causal discourse markers, noting their respective polarity and direction, and temporal discourse markers, noting their direction in the case of relative markers (e.g., relative dates or time frames). The pharmacovigilance system 100 may also identify and mark any optional parameters, for example, those indicating a severity, certainty, course or state, similarly noting their respective polarity and classification. Following this processing, each sentence S will have optional temporal and causal discourse markers and optional parameters, with classification and polarity, and the sentence S can be represented as:

$$S=[\{SC_i\},V,\{D\},\{OP_i\}] \quad \text{Eq. 1}$$

where the sentence S is a function of the primary verb predicate (V), the set of semantic class instances ($SC_i$), the set of discourse parameters (D), and the set of optional parameters ($OP_i$).

The pharmacovigilance system 100 may then proceed with relationship matching and extraction. This may involve identifying the primary verb of the simplified sentence, and matching a lemmatized form of the primary verb with each verb or predicate in a relationship meta-structure or pattern (e.g., the relationships identified in Table 3). This matching process may be similar to that previously described, and the pharmacovigilance system 100 may produce a matching score for the constituent elements of the relationship meta-structure as well as the relationship as a whole. The pharmacovigilance system 100 may filter the results based on a minimum threshold or some other predetermined criteria, which may result in a short list of potential relationship.

With these potential relationships identified, the pharmacovigilance system 100 may proceed with extracting all valid relationships from sentence S. More particularly, where [$SC_1, SC_2, \ldots SC_n$] represents the different semantic classes in a sentence with predicate P, and [$R_x, \ldots, Rn$] represents the ordered list candidate relationships where predicate P exists, a relationship $R_x$ may be present in the sentence S if there exists a tuple [$SC_a$, P, $SC_b$] that maps to a relationship type $R_x$. If the sentence has only one semantic class present, the pharmacovigilance system 100 may infer a matching semantic class type. In other instances, the pharmacovigilance system 100 may mark the relationship as 'unknown'.

With the valid relationships extracted, the pharmacovigilance system 100 may begin to attach the various discourse parameters to the relationships, where the pharmacovigilance system 100 may apply the following heuristic approach. If the discourse parameter is forward directional and placed at or near the beginning of the sentence (i.e., the location of the discourse parameter), then the discourse parameter covers all relational tuples in the sentence, and if the discourse is forward directional and placed within the sentence, the discourse parameter is associated, or connected, with the relationship having the nearest semantic class ahead of the discourse parameter. Similarly, if the discourse parameter is backward directional and placed at or near the end of a sentence, the discourse parameter is associated with the relationship having the closest semantic class before the discourse parameter. Additionally, if the discourse parameter is backward directional it is associated with the relationship nearest to the discourse parameter, irrespective of where the discourse is placed in the sentence. Furthermore, conditional discourse parameters may serve to connect one relationship, (the antecedent relationship) with one or more other relationships (the consequent relationships). The pharmacovigilance system 100 may also attach causal or temporal notations to a relationship depending on the type of discourse parameter being associated with the relationship. For example, the pharmacovigilance system 100 may note RD+, if the relation R leads to the next relation, +DR, if relation R follows the previous relation, RD−, if relation R follows the next relation, or −DR, if relation R leads the previous relation.

The pharmacovigilance system 100 may further attach the optional parameters to the relationships, and may apply the following heuristic approach. If one of the elements in a relationship is the medical condition semantic class and a severity, course or state parameter exists, the parameter is attached to the relationship. Further, if one of the elements in the relationship is the medical condition semantic class and a certainty parameter is associated with the relationship predicate, the certainty parameter is attached to the relationship. Moreover, if a medical condition semantic class is not present but a drug or procedure semantic class is and a course parameter exists, the course parameter is attached to the relationship. The resulting relationships may be represented as R(S+, S++, S+++), depending on the severity parameter (e.g., mild, medium or acute), where a negation operator (e.g., 'not severe') will decrease the degree of the severity parameter, R(C+, C., C−), depending on the certainty parameter (e.g., positive, speculative or negative), where a negation operator will similarly decrease the degree of the parameter, R(Co., Co+, Co++), depending on the course parameter (e.g., mild, long-running, or sudden), and R(St+, St−), depending on the polarity of the state parameter (e.g., improved or deteriorated). Following this stage of processing, each relationship may be represented as:

R=[$SC_a$,P,$SC_b$,t,op{(+D,−D,D+,D−),(S+,S++,S+++),
(C+,C.,C−),(Co.,Co+,Co++),(St+,St−)}]

where t is a temporal operator, which may be determined based on date and time semantic class members or based on temporal discourse parameters. The pharmacovigilance system 100 may then proceed with creating temporal and causal chains for the occurrence model of the unlabeled text (e.g., the report occurrence model or medical occurrence model).

Referring once more to FIG. 4, the causal and temporal semantic model that is generated by the pharmacovigilance system 100 may be provided to the rules engine 250, which may draw one or more medical and clinical inferences (403). By way of example, in some instances, the pharmacovigilance system 100 may use keywords like "death" to determine that the adverse event is serious, but in other instances, event seriousness may be inferred from the existence of certain key concepts and relationships in the source document. Similarly, preparing or generating a report may involve determining the causal chain for the adverse drug reaction report so that a suspect drug can be identified. Moreover, an association or relationship between the drug and the reaction event may not necessarily imply causation, which may look for both correlation and counterfactual dependence. The rules engine 250 may perform the medical and clinical inferences by applying one or more rules, or a sequence of rules or rule chains. As noted previously, in evaluating the different rule chains, the rules engine 250 may interface with the data virtualization and query engine 230, which may allow the rules engine 250 to access one or more databases 120.

The following high-level pseudo-code provides an illustrative example of one way in which the rules engine 250 may determine that a suspect drug is a primary suspect drug for a given adverse event:

Many Suspect Drugs, One Adverse Event
FOR Each Drug
IF
Adverse Event=known Adverse Reactions ["section48"]
  EMC/Daily Med
Then, Tag: Primary Suspect
ELSE
Unknown Table 4, below, provides narrative examples of different rule chains that the rules engine 250 may employ in performing various inferential tasks. In some instances, the rule chains may be arranged in a strict sequential or hierarchical order, which the rules engine 250 may evaluate accordingly. The rules engine 250 may also facilitate inferential determinations by performing forward and backward chaining.

TABLE 4

| | |
|---|---|
| Patient Identification | The rule may look to see if a 'Patient' semantic object is present, which may be satisfied by a patient ID (e.g., alphanumeric ID) or particular keywords (e.g., 'subject' or 'patient'). |
| Drug Identification | The rule may look to see if a 'Drug' semantic object is present, which may be satisfied by any drug name or code. |
| Event Identification | The rule may look to see if a medical condition is present. |
| Reporter Identification | The rule may look to see if a 'Reporter' semantic object is present, which may be satisfied by a reporter ID (e.g., alphanumeric ID). |

TABLE 4-continued

| | | |
|---|---|---|
| Case Seriousness Determination | The rule may determine the seriousness of the adverse event, and may look to see if: | Identified As: |
| | 1) the adverse event is expressly identified as "serious" | Serious |
| | 2) a 'death' semantic object is present, which may be satisfied by the presence of keywords (e.g., died or deceased) or the value of form elements (e.g., a checkbox) | Death |
| | 3) a 'life-threatening' semantic object is present, which may be satisfied by the presence of certain keywords | Life Threatening |
| | 4) the adverse event belongs to the System Organ Class (SOC) of 'congenital deformity' | Serious |
| | 5) an 'outcome' semantic object, with a "hospitalized" value is present, and a 'duration' semantic object, having certain values (e.g., "overnight", "for a day", or ">24 hours"), is present | Serious |
| | 6) a 'critical care' semantic object, which may be satisfied by certain keywords (e.g., "visited critical care"), and a 'duration' semantic object, having certain values (e.g., "overnight", "for a day", or ">24 hours"), is present | Serious |
| | 7) an 'outcome' semantic object, with a "deformed" or "disabled" value, is present | Serious |
| | 8) the adverse event belongs to the Important Medical Event Terms (IME) list | Other |
| Medical Condition Categorization Adverse Events | The rule may determine if the medical condition should be identified as an adverse event, indication, or history. With regards to an adverse event, the rules may look to see if a 'medical condition' semantic object occurs after a 'suspect' drug intake (which itself may be identified by a different rule or set of rules). Each identified 'medical condition' is treated as an event. The rule may also implement a temporal window based on the context (e.g., limiting the 'after' period for clinical trials to 30 days) | |
| Drug Indication | With regards to a drug indication, the rules may look to see if certain causal discourse elements are present, which may be satisfied by keywords (e.g., "drug was taken for" or "to treat"), The rule may also look to see if the medical condition is expressly identified as a drug indication. | |
| Medical History | With regards to a medical history, the rule may look to see if the term "history" and a 'temporal' semantic object are present alongside the medical condition being tested. The rule may also look to see if medical history is expressly mentioned (e.g., in a "medical history" section). | |
| Drug Categorization (Primary, Secondary, Concomitant, Treatment, etc.) | The rule may determine how to categorize one or more drugs of interest (i.e., as a primary or secondary), and may look to see if: | |
| | 1) The drug is expressly categorized (or labeled) using certain keywords (e.g., "primary" or "secondary") | |
| | If no label is present, the rule may look to see if: | |
| | 1) A pair of drugs of interest (A and B) are taken for a given indication (I) | |
| | 2) An event exists for a given indication, which may look to see if an event exists for the drug pair (A and B) in the Summary of Product Characteristics (SPCs) or in the medical literature | |
| |    a. If an event is listed for both drugs, or if drug A and B are the same drug, drug A is identified as a primary suspect | |
| |    b. If an event is listed for A but not B, drug B is identified as a secondary suspect | |
| |    c. If an event is not listed individually for A or B, but is listed collectively for A and B, drug A and B are both identified as secondary suspects | |
| | 3) There is another on-going medical condition (J) (i.e., a condition having previously occurred or occurring in parallel) or another drug of interest (C) | |
| |    a. If no event is found to exist, the drug (C) is identified as a concomitant drug | |
| | 4) There is another drug (D) that was started after the event for a given indication was observed, which is identified as a treatment drug | |

TABLE 4-continued

| | |
|---|---|
| Expected Adverse Event Determination | The rule may determine whether an adverse event was expected, and may look to see if:<br>1) The event was expressly identified as expected using certain keywords<br>If not expressly identified, the rule may look to see if:<br>1) The adverse event matches a list of drug reactions and undesirable effects (e.g., identified from label information, SPCs, or medical literature) for primary or secondary drug suspects, and if a match is found the adverse event is determined to be expected<br>2) The adverse event matches with an elimination route (e.g., identified from label information, SPCs, or medical literature), and if the SOC of the adverse event aligns with the elimination route, the event is determined to be expected<br>3) And if no match exists, the event is determined to be unexpected |
| Related Adverse Event Determination | The rule may determine whether an adverse event was related, and may look to see if:<br>1) The event was expressly identified as related using certain keywords<br>If not expressly identified, the rule may look to see if:<br>1) The adverse event was expected, in which case the event is determined to be related<br>2) If the event matches signals (e.g., warnings, precautions, contra-indications identified from label information, SPCs, or medical literature), then the event is determined to be related |
| Signal Generation | The rule may determine whether an adverse event is a signal, and may look to see if:<br>1) The event was expressly identified as a signal using certain keywords<br>If not expressly identified, the rule may look to see if:<br>1) The adverse event is in a list of warnings, precautions, or contra-indications (e.g., identified from label information, SPCs, or medical literature), then the adverse event is determined to be a signal |
| Pregnancy/Lactating | The rule may determine whether an adverse event presents pregnancy considerations, and may look to see if:<br>1) The event was expressly related to the pregnancy through the use of keywords (e.g., "pregnant" or "expecting mother")<br>2) And for each primary or suspected drug, determine if the label information, SPCs, or medical literature provide a pregnancy sub-section or use certain keywords (e.g., "transmitted through placenta")<br>   a. If the adverse event resulted in an abnormal pregnancy outcome, a new case may be generated for the fetus<br>   b. If a case is generated for the fetus, the route of administration may be determined to be trans-placental<br>3) The event indicates that a father (e.g., through keywords "father" or "male partner") is exposed to a drug, and the pregnancy results in an abnormal outcome, the drug is determined to be a suspect drug<br>The rule may also determine whether an adverse event presents lactating considerations, and may look to see if:<br>1) The event was expressly related to lactating through the use of keywords (e.g., "lactating" or "breastfeeding")<br>2) If the mother and child have adverse events, a new case is generated<br>3) If the child has an adverse event but not the mother, the route of transmission is determined to be breast feeding and the suspect drug is determined to be the drug taken by the mother |

The pharmacovigilance system 100 may use the causal and temporal semantic model and the medical and clinical inferences to generate a structured representation of natural language text stored as a canonical data structure 306. This canonical data structure 306 may be presented to one or more users of the pharmacovigilance system 100 through the ITAP interfaces 275, which may allow the users to modify and/or validate the natural language text, as described above.

The canonical data structure 306 may then be used to automatically generate a narrative report, according to an ADR report template (404). The template may include sections describing the source of the medical record that was processed by the pharmacovigilance system 100 in generating the report, which may include information identifying the case (e.g., case identifier), describing the type of report that is being submitted (e.g., an initial or follow-up), and the date on which the medical record was received. The template may also describe demographic information regarding the patient identified in the medical record, including, for example, the age of the patient along with the patients gender and ethnicity. The template may also include a section describing the relevant medical history of the patient, and may also include an identification of possible concomitant medications that the patient was taking at the time of the adverse reaction.

The generated report may include a section identifying the suspect drug, the indication for which it was taken, and the dosage of the drug that the patient was taking and the duration for which the patient was taking it. The template may also identify the adverse event that was experienced, including, for example, the onset date and duration after which the patient started on the drug, along with a description of the reaction experienced by the patient. The template may also include a section noting if the event was considered serious. The generated report may also include a section describing the action that was taken regarding the suspect drug, for example, if the drug dosage was reduced or if the drug was stopped altogether. It may also state whether a causal link is believed to exist between the adverse event and the patient's treatment using the drug. The report may then conclude with the ultimate outcome of the event and the date on which this occurred.

The pharmacovigilance system 100 may take similar actions as described above when processing medical literature abstracts, but may apply a relatively streamlined approach and may only look to identify a subset of the semantic classes and relationships (e.g., patient, drug, manufacturing or reporting country, reporter). For example, in order to determine where the case should be reported the pharmacovigilance system 100 may look for a drug of interest and a manufacturing country, so as to determine where the case should be reported. The pharmacovigilance system 100 may apply a relatively simpler set of rules to determine if the document is worth investigating further. If upon further investigation a determination is made that enough information is contained within the article to qualify as a case, the entire article may be processed in a manner similar to that described above.

Use of the pharmacovigilance system 100 as just described may facilitate early detection of previously unidentified safety problems, detection of increases in frequency, identification of risk factors, quantification of the risks, preventing patients from unnecessary complications by providing faster guidance, and providing automatic notifications.

Figure 8:
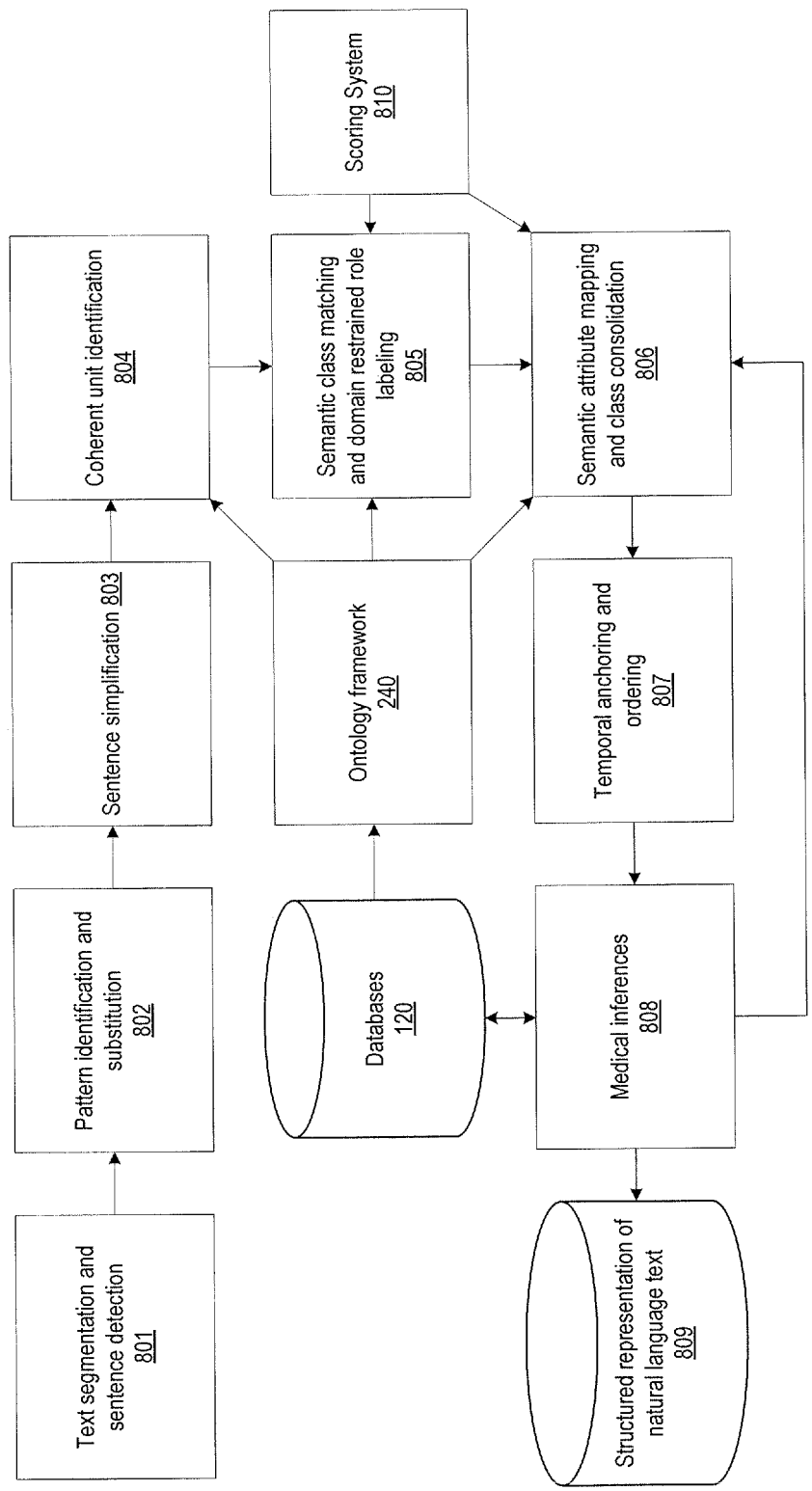
FIG. 8 depicts some of the logic that may be performed by the pharmacovigilance system.

FIG. 8 describes, in greater detail, some of the logic that may be performed by the pharmacovigilance system 100. As noted above, the pharmacovigilance system 100, through the NLP pipeline 220, may perform one or more language processing functions. The pharmacovigilance system 100 may detect sentences in the structured or unstructured data and may segment the data accordingly (801). The pharmacovigilance system 100 may take advantage of functionality provided by cTAKES in order to perform the sentence detection and segmentation 221 (801). The NLP pipeline 220 may also perform certain pre-processing functions, including, for example, abbreviation expansion and regular expression based pattern identification and substitution (802). The NLP pipeline 220 may also perform sentence simplification employing syntactic analysis, which may involve multi-sentence modeling. The syntactic analysis performed by the NLP pipeline 220 may be able to handle sentence level conjunctions, noun phrase conjunctions, and various punctuation markers. The NLP pipeline 220 may also parse the data into chunks and identify coherent text units (804). The NLP pipeline 220 may take advantage of functionality provided by cTAKES in order to perform coherent unit identification 224 (804).

The pharmacovigilance system 100 may also process the data and match coherent units to one or more semantic classes or semantic relations, e.g., those mentioned in Table 2 and 3 (805). In instances where the semantic class has different sub-classes or attributes, the pharmacovigilance system 100 may also match coherent units to these attributes, and may further specify if an attribute is not present (i.e., could not be found or matched), by using a 'null' or 'unknown' identifier. This processing may involve performing named entity recognition (NER), which may serve to extract information from the textual data and associate the data with a semantic class. In so doing, the pharmacovigilance system 100 may interface with the ontology framework 240, and may draw upon one or more lexical ontologies 241, e.g., Wordnet or UMLS (Unified Medical Language System) semantic network, or custom ontologies 242, which may in turn rely on one or more databases 120. The UMLS semantic network is a compendium of various controlled vocabularies in the biomedical sciences, which provides a mapping structure among these vocabularies to permit translation among the various terminology systems. The UMLS semantic network was designed by and is maintained by the US National Library of Medicine. Furthermore, as a coherent unit may not perfectly match or map to a semantic class or semantic relationship, the pharmacovigilance system 100 may use a scoring system 810, which may be used to select the best match for the text. Additionally, or alternatively, the score produced by the scoring system 810 may serve as a threshold value for determining a match between a semantic class and coherent unit. In some cases, pharmacovigilance system 100 may utilize the score to determine whether user validation is required, for example, if the score is very low or if the match cannot be disambiguated. In such situations, the pharmacovigilance system 100 may prompt the user to identify or disambiguate the match, for example, using the ITAP interfaces 275 as described above.

The scoring system 810 used by the pharmacovigilance system 100 may involve evaluating the syntactic and semantic similarity of the coherent unit against seeded keywords and seeded keyword patterns, and may also use part of speech (POS) tag based patterns in the evaluation process. The scoring system 810 may assess the suitability of a term as being the argument for a predicate. The scoring system 810 may also look at the target being evaluated in context, which may look for the presence of certain operators or other keywords and/or look for the presence of other semantic classes, which may themselves be weighted by their respective matching score. The pharmacovigilance system 100 may optionally implement a bootstrapping method, and may continuously update word patterns, which may increase the systems accuracy and efficiency in future matching processes.

The pharmacovigilance system 100 may also perform domain restrained semantic role labeling (805). This may involve performing lexical and semantic matching against a discrete set of identified predicates, for example, those predicates identified in the UMLS semantic network or those provided in the relationships described in Table 3, above. This process may also involve identification of the main verb in a sentence, which may serve to further limit the processing domain. The pharmacovigilance system 100 may arrange identified semantic classes identified as arguments of the predicate such that the matching score is maximized.

Moreover, the pharmacovigilance system 100 may identify the presence of one or more semantic classes, and one or more semantic relationships. It may be possible for a coherent unit to contain more than one semantic relationship, which may share common semantic classes. For example, a given sentence or coherent unit may satisfy relationship R5 and R11 (Table 3); a relationship may exist not only between a first medical condition and a second medical condition (R5) but also between the first medical condition and a part of the anatomy (R11). It may also be possible that an identified semantic class may not enter into, or be associated with, a valid semantic relationship.

The pharmacovigilance system 100 may map text tokens present in the unlabeled text to semantic class attributes (806). The pharmacovigilance system 100 may also use a scoring methodology in this process, which may identify a match based on a syntactic and semantic similarity to seeded keywords of semantic class attributes. The NLP pipeline 220 may also take into account certain modifiers, e.g., numerical modifiers or adjectives, which may have to be clubbed for multi token units.

The pharmacovigilance system 100 may also perform semantic class consolidation by performing anaphora resolution (806). This process may evaluate whether a semantic class or relationship has been correctly identified by viewing the expression in context. The evaluation process may implement a scoring mechanism based on the global context of the document, an identification of agreeing and conflicting attributes, and the relationship type at issue, which may be based on the semantic class of the verb contained therein.

The pharmacovigilance system 100 may perform temporal ordering of sentences in which relationships have been identified. The pharmacovigilance system 100 may perform temporal ordering for all sentences containing an identified semantic relationship, or may selectively order those sentences which contain a particular subset of relationships (807). The pharmacovigilance system 100 may perform this ordering based on the appearance of the relationship in the text as a whole and/or based on the presence of prepositional connectives. The pharmacovigilance system 100 may also perform temporal ordering based on the presence of discourse connectives present in the Penn Discourse Treebank (PDTB) or Biomedical Discourse Relation Bank (BioRDB), which is a derivative of PDTB. As noted above, the pharmacovigilance system 100 may also infer possible causal chains by assessing relationships between different sentences based on the presence of temporal discourse connectives.

Figure 9:
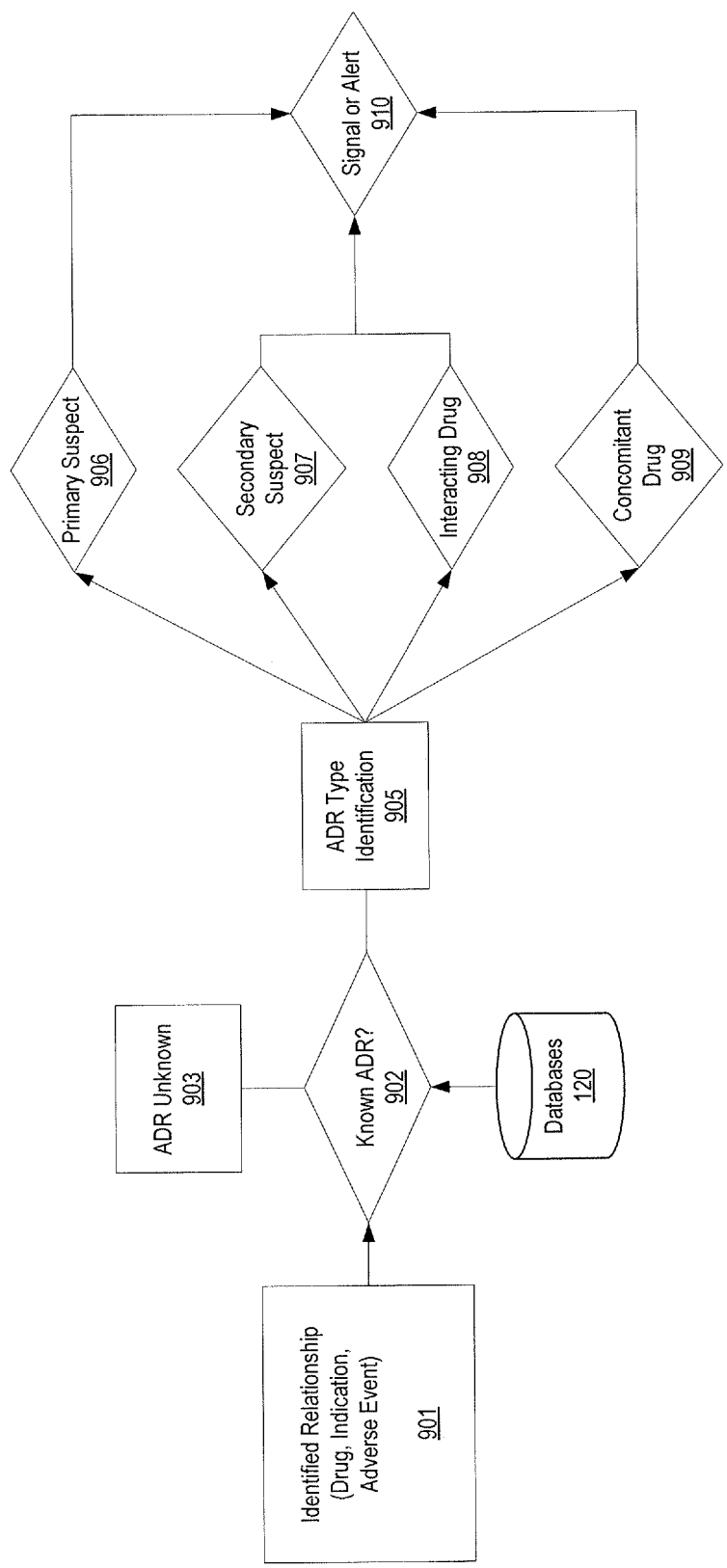
FIG. 9 depicts an example of a rule chain that a rules engine may apply in making a causality assessment.

The pharmacovigilance system 100 may utilize the rules engine 250 to apply rules to the causal inference chains that are identified in order to arrive at a clinical or medical inference (808). For example, the pharmacovigilance system 100 may determine categorize medical conditions and drug reactions or determine case seriousness. The pharmacovigilance system 100 may also perform a causality assessment with regards to an adverse reaction event, which may include determining if a reaction was expected and generating an appropriate reaction event signal and/or alert. With reference to FIG. 9, for example, the pharmacovigilance system 100 may provide inputs to the rules engine 250 corresponding to a causal chain that is to be tested (901). For example, the pharmacovigilance system 100 may have identified a relationship between a drug, an indication for the drug, and an adverse event. The pharmacovigilance system 100, through the rules engine 250, may assess whether the adverse reaction was known based on the drug's use for the provided indication (902). In doing so, the pharmacovigilance system 100 may communicate with one or more databases 120, e.g., the curated reference and clinical knowledge databases 122 and coding databases 123, to determine if a relationship has been previously identified. If no entry is found, the pharmacovigilance system 100 concludes that the cause of the adverse reaction is unknown (903). Alternatively, if a result is found, the pharmacovigilance system 100 may then attempt to identify the type of adverse drug reaction that occurred (905). The pharmacovigilance system 100 may look to see whether the drug is identified as a primary suspect (906), a secondary suspect (907), an interacting drug (908), or a concomitant drug (909). The pharmacovigilance system 100 may also determine whether a signal or alert needs to be generated (910).

The pharmacovigilance system 100 may utilize the above described processing to generate a structured representation of the natural language text contained in the original source document (809).

Figure 13:
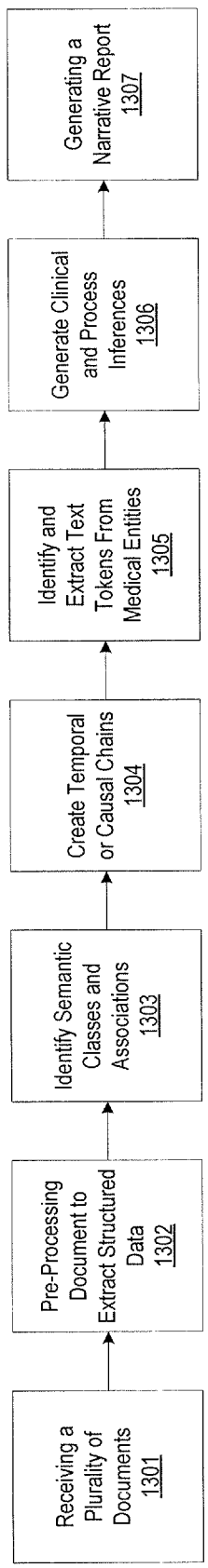
FIG. 13 illustrates one example of the overall operation of the pharmacovigilance system.

FIG. 13 provides an example of how the pharmacovigilance system 100 may operate to identify adverse drug reactions and to improve drug safety surveillance.

The pharmacovigilance system 100 may receive various disparate source documents, which may contain structured or unstructured data in a number of different formats (1301). The pharmacovigilance system 100 may receive these documents through the data virtualization and query engine 230, which may retrieve the records from medical records databases 121.

The pharmacovigilance system 100 may pre-process the source documents to extract the structured data and unstructured data, and to convert the data to a standard canonical format (1302). This pre-processing may make use of the NLP pipeline 220. The converted canonical data may also be processed by the NLP pipeline 220 to identify various semantic classes and semantic associations among the semantic classes (1303). In so doing, the NLP pipeline 220 may interface with the ontology framework 240, which may also communicate with the data virtualization and query engine 230 to leverage information contained in the medical databases 120.

The pharmacovigilance system 100 may use the identified semantic classes and semantic associations to create temporal models or chains, which order the information and events described in the source documents in a temporal manner (1304). The pharmacovigilance system 100 may also use the identified semantic classes and semantic associations to create causal textual chains, which may, for example, provide an association between a drug which is taken, an actual event of drug consumption, and a subsequent drug reaction (1304).

The pharmacovigilance system 100 may also identify and extract both medical and non-medical text tokens associated with or corresponding to various medical entities (1305). The medical text tokens may, for example, correspond to a drug identification, a medical condition, a medical device, a medical procedure, and an anatomical identifier. The non-medical text tokens may similarly correspond to a date, an organization, and a person. The pharmacovigilance system 100 may identify the medical and non-medical text tokens based on heuristic and semantic mapping. In doing so, the pharmacovigilance system 100 may also draw upon a standardized medical database 120.

The pharmacovigilance system 100 may also use the temporal textual chains and the causal textual chains to generate clinical and process related inferences (1306). The pharmacovigilance system 100 may interface with the data virtualization and query engine 230 to retrieve information from various backend medical databases and knowledge sources 120. The pharmacovigilance system 100 may also utilize information provided by the ontology framework 240 in forming the clinical and process related inferences.

The pharmacovigilance system 100 may use all of the previous determined and generated information to generate a narrative report based on chronological events (1307). The report may describe physical intervention events and clinical events corresponding to the text tokens.

The pharmacovigilance system 100 may be implemented in hardware, software, firmware, or any combination of hardware, software, and firmware, and may or may not reside within a single physical or logical space. For example, the modules or subsystems referred to in this document and which may or may not be shown in the drawings, may be remotely located from each other and may be coupled by a communication network.

Figure 12:
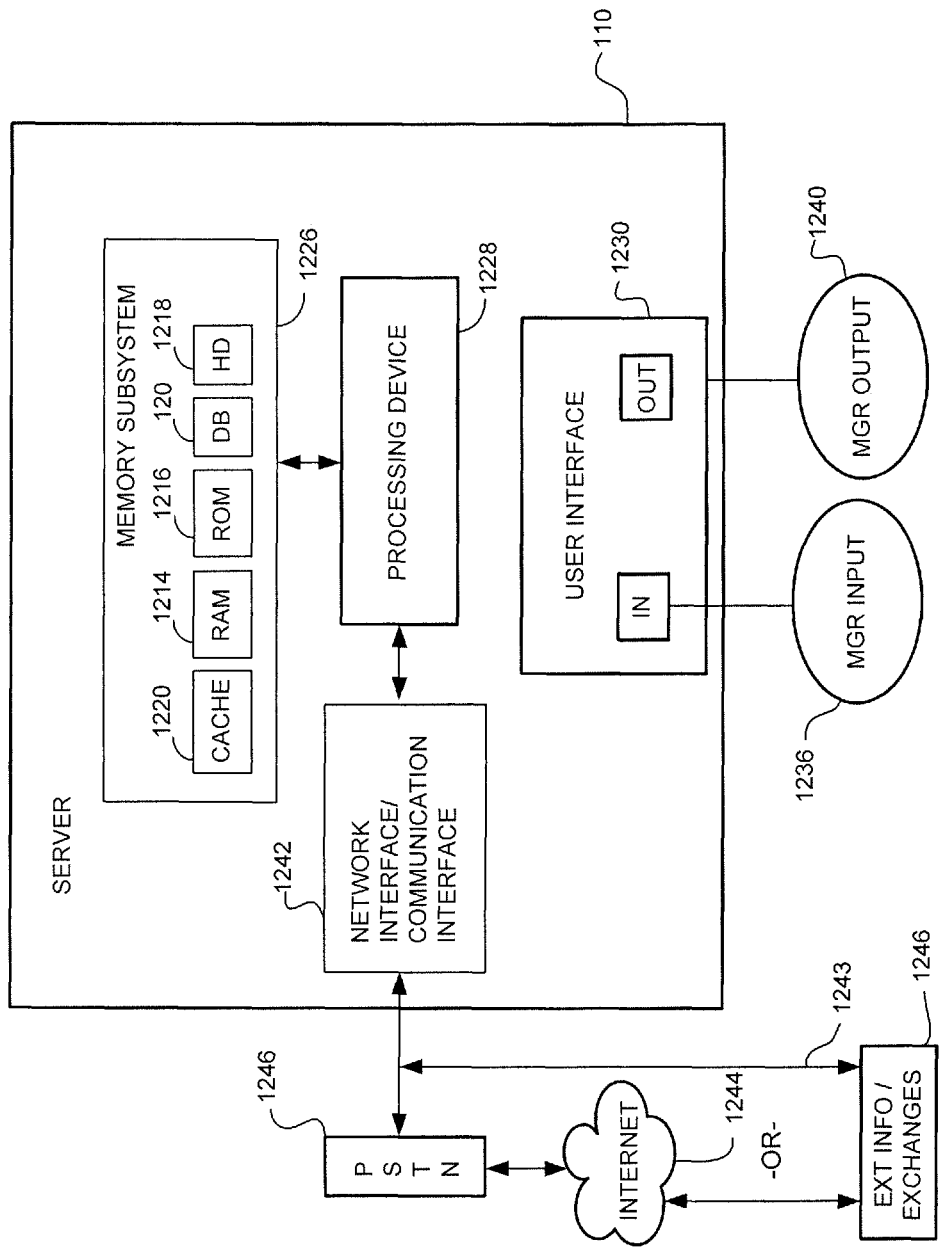
FIG. 12 is a schematic of a representative server that the pharmacovigilance system may employ.

With reference to FIG. 12, a server 110 in the pharmacovigilance system 100 may be a personal computer, server, or other suitable computer, and may include various hardware components, such as RAM 1214, ROM 1216, hard disk storage 1218, cache memory 1219, one or more databases 120, and the like (also referred to as "memory subsystem 1226"). The server 110 may include any suitable processing device 128, such as a computer, microprocessor, RISC processor (reduced instruction set computer), CISC processor (complex instruction set computer), mainframe computer, work station, single-chip computer, distributed processor, server, controller, micro-controller, discrete logic computer, and the like, as is known in the art. For example, the processing device 1228 may be an Intel Pentium® microprocessor, x86 compatible microprocessor, or equivalent device, and may be incorporated into a server, a personal computer, or any suitable computing platform.

The memory subsystem 1226 may include any suitable storage components, such as RAM, EPROM (electrically programmable ROM), flash memory, dynamic memory, static memory, FIFO (first-in, first-out) memory, LIFO (last-in, first-out) memory, circular memory, semiconductor memory, bubble memory, buffer memory, disk memory, optical memory, cache memory, and the like. Any suitable form of memory may be used, whether fixed storage on a magnetic medium, storage in a semiconductor device, or remote storage accessible through a communication link. A user or system manager interface 1230 may be coupled to the server 110 and may include various input devices 1236, such as switches selectable by the system manager and/or a keyboard. The user interface also may include suitable output devices 1240, such as an LCD display, a CRT, various LED indicators, a printer, and/or a speech output device, as is known in the art.

To facilitate communication between the computer system 100 and external sources, a communication interface 1242 may be operatively coupled to the computer system. The communication interface 1242 may be, for example, a local area network, such as an Ethernet network, intranet, Internet, or other suitable network 1244. The communication interface 1242 may also be connected to a public switched telephone network (PSTN) 1246 or POTS (plain old telephone system), which may facilitate communication via the Internet 1244. Any suitable commercially available communication device or network may be used.

The logic, circuitry, and processing described above may be encoded or stored in a machine-readable or computer-readable medium such as a compact disc read only memory (CDROM), magnetic or optical disk, flash memory, random access memory (RAM) or read only memory (ROM), erasable programmable read only memory (EPROM) or other machine-readable medium as, for examples, instructions for execution by a processor, controller, or other processing device.

The medium may be implemented as any device that contains, stores, communicates, propagates, or transports executable instructions for use by or in connection with an instruction executable system, apparatus, or device. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

In other implementations, the logic may be represented in a signal or a propagated-signal medium. For example, the instructions that implement the logic of any given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of a single program, separate programs, or distributed across several memories and processors.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A system comprising:
a server comprising a processor, memory coupled with the processor, a plurality of databases coupled with the processor, and a data interface;
the memory having stored thereon processor executable instructions comprising data virtualization and query instructions, ontology framework instructions, search framework instructions, natural language processing pipeline instructions, and rules engine instructions, where
the data virtualization and query instructions, when executed by the processor, cause communication with the plurality of databases, the databases including:
a medical record database, where the medical record database contains medical records,
a curated reference and clinical knowledge database, a causal and temporal model database, and a curated drug safety and case database,
wherein the ontology framework instructions cause the processor to build and manage a custom ontology;
the search framework instructions cause the processor to provide search capabilities for the system,
wherein the natural language processing pipeline instructions, the ontology framework instructions, and data virtualization and query instructions cause the processor to:
automatically detect an update to at least one of the medical records;
access unstructured textual data from the at least one of the medical records stored in one or more of the medical record database and curated reference and clinical knowledge database;
identify semantic classes for terms in the unstructured textual data by matching the terms in the unstructured textual data to attributes associated with the semantic classes, wherein the semantic classes comprise a medical substance class, a medical condition class, and a time class, the time class representative of a time value term included in the unstructured textual data, wherein a medical substance term associated with the medical substance class and a medical condition term associated with the medical condition class are in different sentences of the unstructured textual data;
obtain relationship patterns associated with semantic relationships from the curated reference and clinical knowledge database;
identify one or more semantic relationships in the unstructured textual data by matching one or more identified semantic classes to at least one of the relationship patterns;
identify one or more discourse parameters in the unstructured textual data, where the discourse parameter includes one or more temporal discourse parameters indicative of a temporal order of the medical substance term and the medical condition term in the different sentences of the unstructured textual data with respect to the time value term, wherein the discourse parameter does not include the time value term;
generate a causal and temporal model of the unstructured textual data, the causal and temporal model comprising a list of notation markers and temporal markers arranged in a structured format, the notation markers representative of the identified semantic relationships, the temporal markers indicative of the temporal order of the terms in the different sentences of the unstructured textual data, the temporal markers attached to the notation markers; and
store the causal and temporal model in the causal and temporal model database, and
wherein the rules engine instructions and the data virtualization and query instructions cause the processor to:
access the causal and temporal model from the causal and temporal model database; and
determine a clinical event based on execution of a plurality of rule instructions linked together, wherein each of the rule instructions cause the processor to:
access the list of notation markers and temporal markers of the causal and temporal model;
determine the list of notation markers and temporal markers of the causal and temporal model match a pattern of notation markers and temporal markers; and
select the clinical event from a plurality of predetermined clinical event classifications in response to the list of notation markers and temporal markers of the causal and temporal model matching the predetermined pattern of notation markers and temporal markers; and
wherein the data interface comprises intelligent text analysis platform instructions, stored in memory, that, when executed by the processor, cause the processor to, in response to detection of the update to the at least one of the medical records and determination of the clinical event:
generate an intelligent text analysis user interface, the intelligent text analysis user interface comprising a temporal chain user interface, the temporal chain user interface comprising a plurality of medical labels descriptive of the identified semantic relationships, the medical labels sequentially arranged on the temporal chain user interface based on the temporal markers of the causal and temporal model; and
transmit the user interface to a display device for a user assigned to the medical record.

2. The system of claim 1, where the natural language processing pipeline instructions cause the processor to convert the medical information into a standard canonical format, and process the unstructured textual data of the medical information in the standard canonical format to generate the causal and temporal model.

3. The system of claim 1, where, in order to generate the causal and temporal model, the natural language processing pipeline instructions further cause the processor to:
identify a causal discourse parameter in the unstructured textual data representative of a causal relationship between the terms in the unstructured textual data;
attach a casual marker to the at least one of the notation markers, the causal marker corresponding to the causal discourse parameter; and
determine an occurrence model for the identified semantic relationships, where the occurrence model includes a combination of the notation markers, temporal markers, and causal markers; and
generate the causal and temporal model based on the occurrence model, where the causal and temporal model comprises one or more causal chains inferred based on the combination of the notation markers, temporal markers, and causal markers included in the occurrence model.

4. The system of claim 3, where, in order to generate the causal and temporal model, the natural language processing pipeline instructions further cause the processor to connect an antecedent semantic relationship with a consequent semantic relationship when the discourse parameter is a conditional discourse parameter.

5. The system of claim 1, where, in order to generate the causal and temporal model, the natural language processing pipeline instructions further cause the processor to:
identify an additional discourse parameter in the unstructured textual data, where the additional discourse parameters comprise a severity parameter having a degree, a certainty parameter having a polarity, a course parameter reflecting a nature of treatment, a state parameter reflecting a current state, or a combination thereof; and
attach an additional marker to the at least one of the semantic markers, the additional marker corresponding to the additional discourse parameter.

6. The system of claim 1, where:
the curated reference and clinical knowledge database includes medical information to be processed, a coding base contains information regarding drug classifications under one or more classification systems, and the curated drug safety and case database contains information regarding reactions experienced by patients consuming a drug;
the natural language processing pipeline instructions further cause the processor to identify at least a patient semantic class, an adverse reaction semantic class, a predicate semantic class, a drug semantic class, an indication semantic class and a drug dosage semantic class; and
the clinical determinations include one or more of a case admissibility and validity determination, a medical condition categorization, a drug reaction categorization, a case serious determination, an expected reaction determination, and a relatedness determination.

7. The system of claim 1, where the data virtualization and query instructions further cause the processor to detect addition of an additional medical record to the medical record database and the natural language processing pipeline when executed by the processor automatically processes the additional medical record.

8. The system of claim 1, where, in order to process the unstructured textual data of the medical information, the natural language processing pipeline instructions further cause the processor to perform one or more of text segmentation and sentence detection, pattern identification and substitution, sentence simplification, and coherent unit identification.

9. The system of claim 8, where the natural language processing pipeline instructions, in order to process the unstructured textual data of the medical information, further cause the processor to perform one or more of domain restrained role labeling, semantic attribute mapping and class consolidation, temporal anchoring and ordering, and causal relationship identification.

10. The system of claim 1, where, in order to identify the semantic classes for terms in the unstructured textual data, the natural language processing pipeline instructions further cause the processor to:
process the unstructured textual data to form one or more coherent chunk units;
match the one or more coherent chunk units to a matching semantic class based on a part-of-speech similarity, a seed word similarity, a syntactic pattern similarity, or combination thereof; and
generate a matching score for each of the one or more coherent chunk units, and when the matching score is below a threshold value or other predetermined criteria flags the coherent chunk unit for user disambiguation.

11. The system of claim 10, where the natural language processing pipeline instructions further cause the processor to:
match the one or more identified semantic classes to one or more relationship arguments in a particular relationship pattern, and generate a relationship matching score for each relationship argument and for the particular relationship pattern; and infer a matching relationship based on the relationship matching scores.

12. The system of claim 1, where the intelligent text analysis user interfaces further comprise a semantic class identification tool interface, wherein the semantic class identification tool interface provides, on a computer display device, a list of the one or more identified semantic classes, where the list comprises constituent coherent chunk units and associated matching scores, and a graphical overlay that allows the user to select one or more coherent chunk units to associate with a user specified semantic class; and
where the semantic relationship identification tool interface provides, on the computer display device, a list of the identified semantic relationships, where the list comprises constituent relationship arguments and an associated matching score, and a graphical overlay that allows the user to select one or more relationship arguments to associate with a user specified semantic relationship.

13. A computer-implemented method comprising:
accessing a medical record database, at a server having a data processor and a memory in communication with the data processor, where the medical record database contains medical records,
detecting an update to at least one of the medical records in the medical records database;
in response to detection of the update to the at least one of the medical records:
accessing unstructured textual data from the medical records database;
identifying semantic classes for terms in the unstructured textual data with the data processor by matching the terms in the unstructured textual data to attributes associated with the semantic classes, wherein the semantic classes comprise a medical substance class, a medical condition class, and a time class, the time class representative of a time value term included in the unstructured textual data, wherein a medical substance term associated with the medical substance class and a medical condition term associated with the medical condition class are in different sentences of the unstructured textual data,
identifying one or more semantic relationships in the textual data with the data processor by matching one or more identified semantic classes to a particular relationship pattern, where the relationship pattern comprises one or more relationship arguments,
identifying a discourse parameter in the unstructured textual data, where the discourse parameter includes one or more temporal discourse parameters indicative of a temporal order of the medical substance term and the medical condition term in the different sentences of the unstructured textual data with respect to the time value term, and generating a causal and temporal model of the unstructured textual data, the causal and temporal model comprising a list of notation markers representative of the identified semantic relationships, where temporal markers are positioned adjacent to the notation markers, respectively, the temporal markers indicative of the temporal order of the terms in the different sentences of the unstructured textual data;

determining a clinical event based on execution of a plurality of rule instructions linked together;

executing each of the rule instructions to:
  access the list of notation markers and temporal markers of the causal and temporal model,
  determine the list of notation markers and temporal markers of the causal and temporal model match a corresponding pattern of notation markers and temporal markers, and
  select the clinical event from a plurality of predetermined clinical event classifications in response to the list of notation markers and temporal markers of the causal and temporal model matching the corresponding pattern of notation markers and temporal markers; and providing, by the server over a data interface coupled to the data processor, in response to detection of the updated medical record and determination of the clinical event, one or more intelligent text analysis user interfaces on a computer display device, where the one or more intelligent text analysis user interfaces, comprising a temporal chain user interface, the temporal chain user interface comprising a list of medical labels descriptive of the identified semantic relationships, the medical labels sequentially arranged on the temporal chain user interface based on the temporal markers of the structured representation of natural language text.

14. The method of claim 13, wherein processing the medical information to generate a structured representation of natural language text further comprises:
  identifying a causal discourse parameter in the unstructured textual data representative of a causal relationship between the terms in the unstructured textual data;
  attaching a casual marker to the at least one of the notation markers, the causal marker corresponding to the causal discourse parameter; and
  determining an occurrence model for the identified semantic relationships, where the occurrence model includes a combination of the notation markers, temporal markers, and causal markers;
  wherein the causal and temporal model comprises one or more causal chains inferred based on the combination of the notation markers, temporal markers, and causal markers included in the occurrence model.

15. The method of claim 13, where generating the causal and temporal model further comprises connecting an antecedent semantic relationship with a consequent semantic relationship when the one or more discourse parameters is a conditional discourse parameter.

16. The method of claim 13, where identifying the semantic classes for terms in the unstructured textual data comprises:
  processing the unstructured textual data with the data processor to form one or more coherent chunk units;
  matching the one or more coherent chunk units, with the data processor, to a matching semantic class based on a part-of-speech similarity, a seed word similarity, a syntactic pattern similarity, or combination thereof; and
  generating a matching score for each of the one or more coherent chunk units using the data processor, and when the matching score is below a threshold value or other predetermined criteria, flagging the coherent chunk unit, by the data processor, for user disambiguation.

17. The method of claim 13, where matching one or more identified semantic classes to a particular relationship pattern comprises:
  matching the one or more identified semantic classes, using the data processor to one or more relationship arguments in a particular relationship pattern;
  generating a relationship matching score with the data processor for each relationship argument and for the particular relationship pattern; and
  inferring a matching relationship, using the data processor, based on the relationship matching scores.

* * * * *